United States Patent [19]

Jowett et al.

[11] 3,958,122
[45] May 18, 1976

[54] EXHAUST GAS ANALYZER HAVING PRESSURE AND TEMPERATURE COMPENSATION

[75] Inventors: Terence W. Jowett, Avon, Conn.; Anthony D. M. Knights, Longmeadow, Mass.; Thomas A. Cross, Winsted, Conn.

[73] Assignee: United Technologies Corporation, Hartford, Conn.

[22] Filed: Dec. 19, 1974

[21] Appl. No.: 534,493

[52] U.S. Cl. .............................. 250/346; 250/344; 250/345
[51] Int. Cl.² ........................................ G01N 21/34
[58] Field of Search ............ 250/343, 344, 345, 346

[56] References Cited
UNITED STATES PATENTS

| | | | |
|---|---|---|---|
| 2,876,357 | 3/1959 | Waters | 250/345 |
| 3,103,586 | 9/1963 | Ovrebo et al. | 250/345 |
| 3,728,540 | 4/1973 | Todd et al. | 250/343 |
| 3,731,092 | 5/1973 | Freilino | 250/346 |
| 3,770,974 | 11/1973 | Fertig | 250/346 |

*Primary Examiner*—Archie R. Borchelt
*Assistant Examiner*—B. C. Anderson
*Attorney, Agent, or Firm*—D. F. Bradley

[57] ABSTRACT

The contaminants in the exhaust gas emissions from a motor vehicle such as carbon monoxide (CO) and hydrocarbons (HC) are analyzed and the concentration of the contaminants together with other pertinent data is displayed in a digital manner. The exhaust gas emissions are fed into a sample cell contained within a nondispersive infrared analyzer and the absorption of an infrared radiation beam at selected wavelengths by the gas within the cell is measured. A reference cell containing a reference gas is also positioned in the infrared radiation beam path. By means of a rotating chopper disk positioned in the light path, the infrared radiation beam passes alternately through the reference cell and the sample cell and is focused at a plurality of detectors which are each sensitized to a narrow wave band by a filter and which receive the alternate sample cell and reference cell radiation pulses. Synchronization of the system is provided by a notch in the chopper disk which passes alternately between three light sources and associated photoresponsive devices. Automatic span correction is obtained by an automatic gain control circuit which maintains the reference cell output at a predetermined amplitude. The sample cell is initially filled with ambient air by a gas transport system. By measuring the sample cell and reference cell outputs with ambient air in the sample cell, and then measuring the sample cell and reference cell outputs with exhaust gas in the sample cell, a ratio can be computed which is proportional to the amount of the contaminant. Computation of the ratio in this manner results in automatic zeroing and spanning of the system. The computed ratio is then calibrated for nonlinearities in the system, and linear corrections are made for variations in ambient pressure and for variations in the temperature of the gas passing through the sample tube. Provision is also made for assuring that the vehicle being tested has achieved a predetermined engine speed and that no blockage has occurred in the gas transport system when the measurements are made. After the exhaust gas has been analyzed it is replaced in the sample cell with ambient air to prevent contamination of the system optics from the exhaust gas. A sapphire window is positioned in front of the infrared source to reduce changes in source temperature by air currents produced by the rotating chopper disk.

11 Claims, 17 Drawing Figures

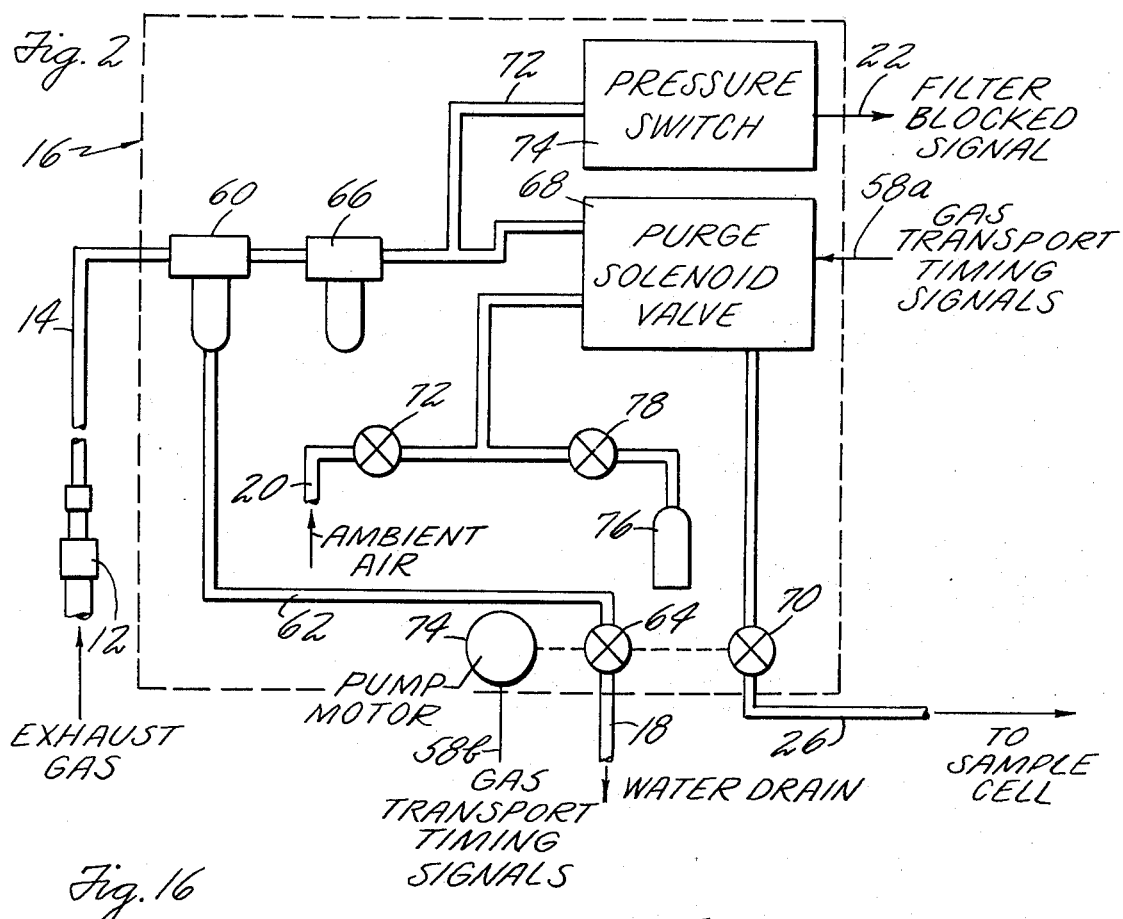
Fig. 2
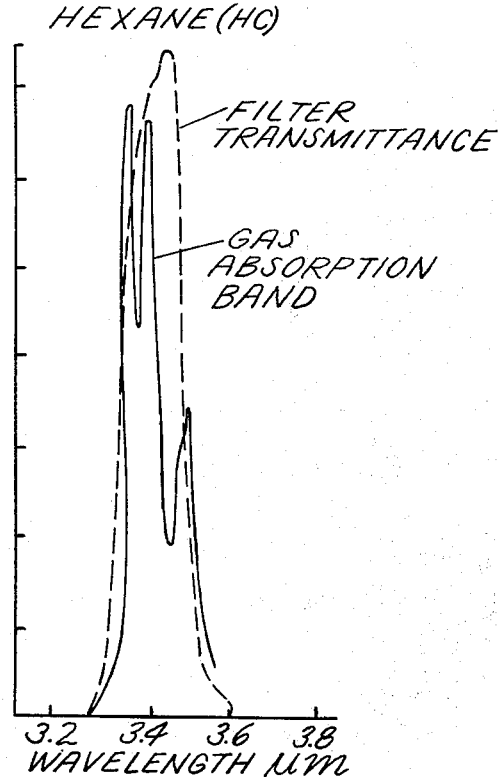
Fig. 16 HEXANE (HC)
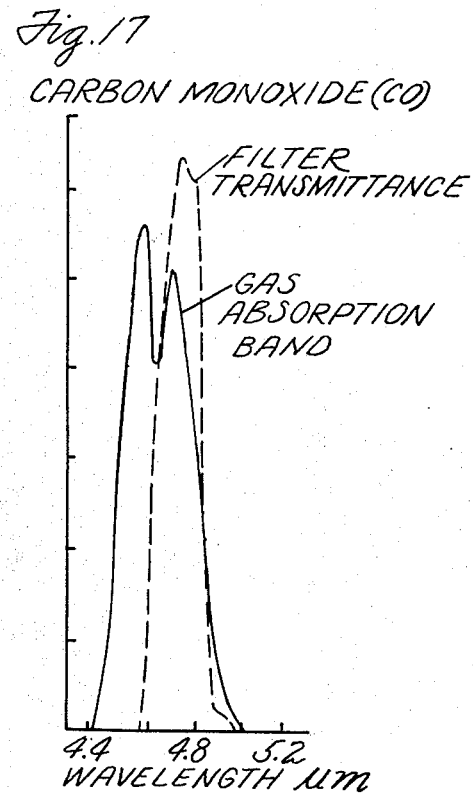
Fig. 17 CARBON MONOXIDE (CO)

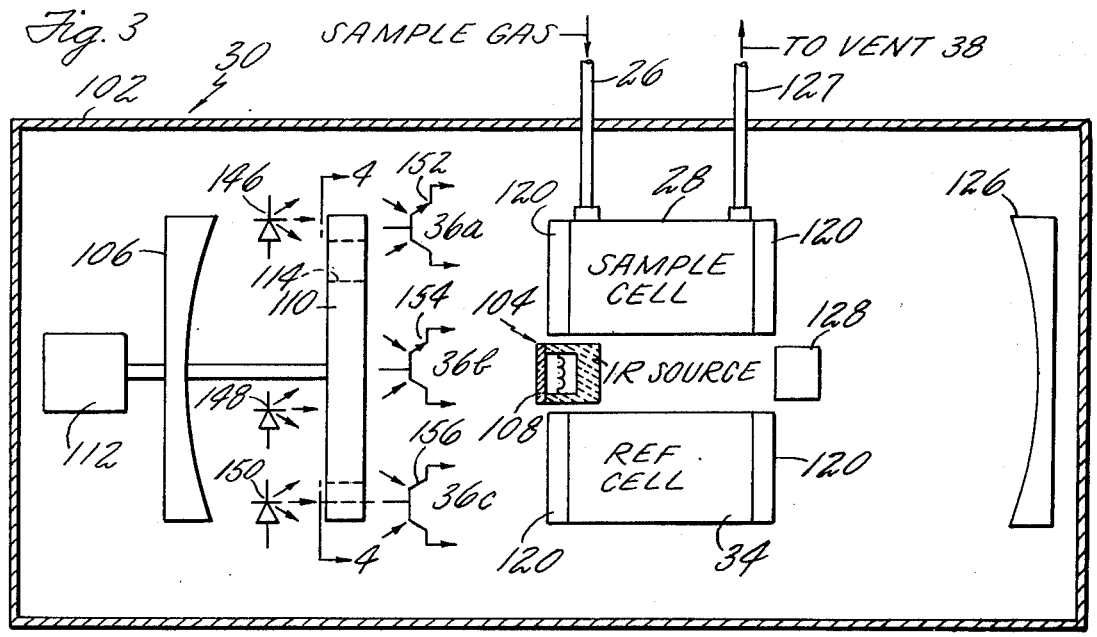
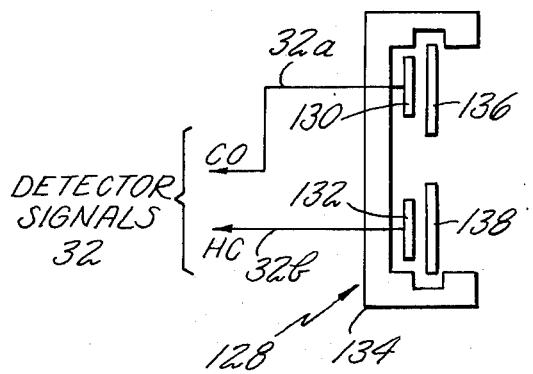
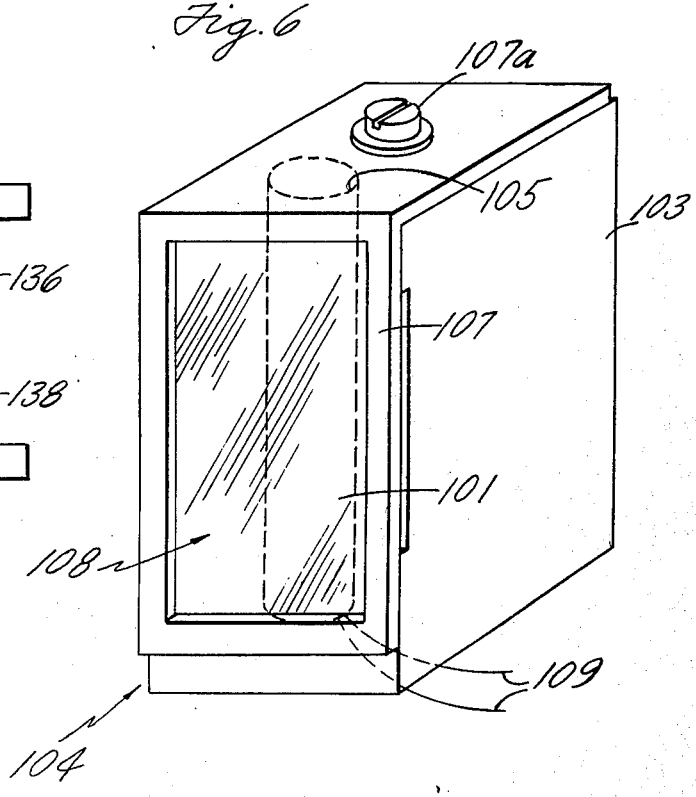

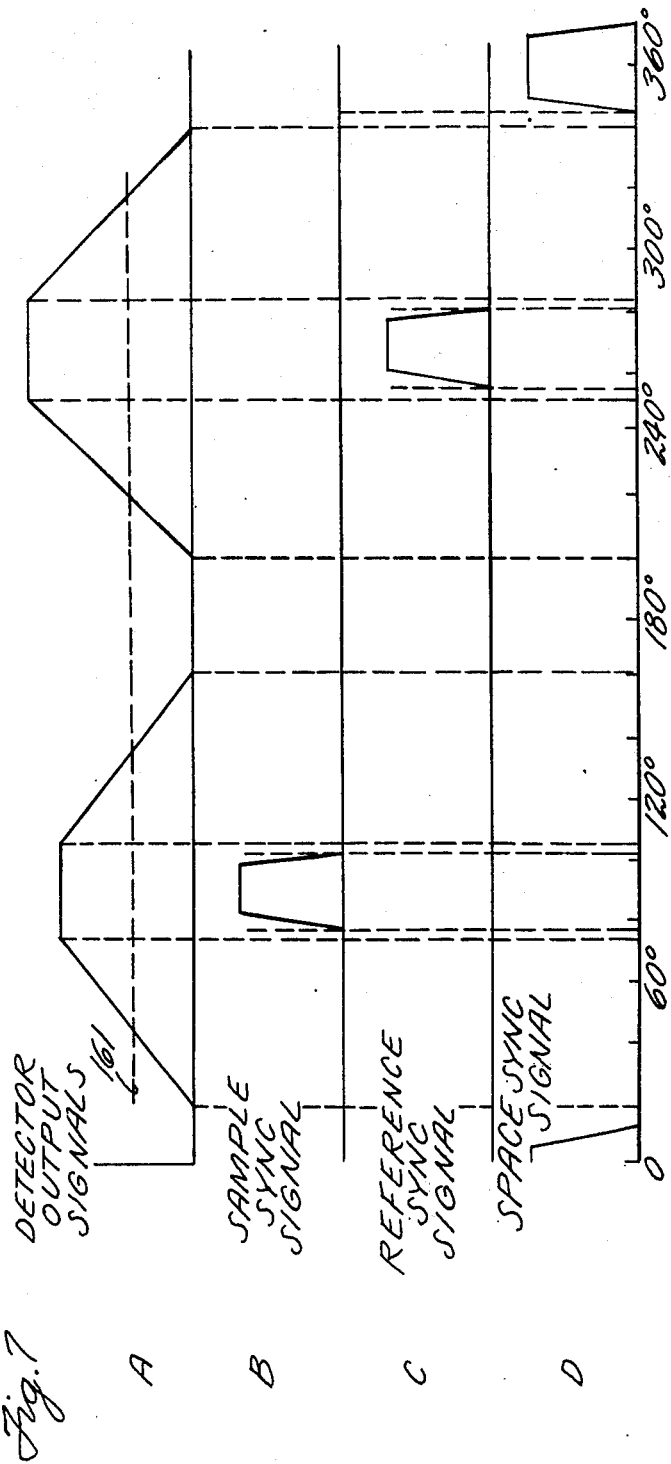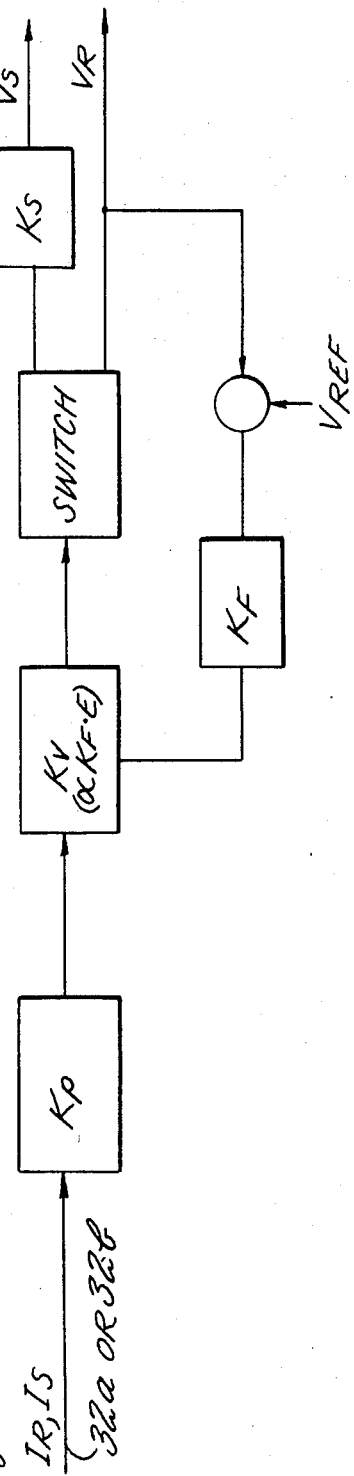

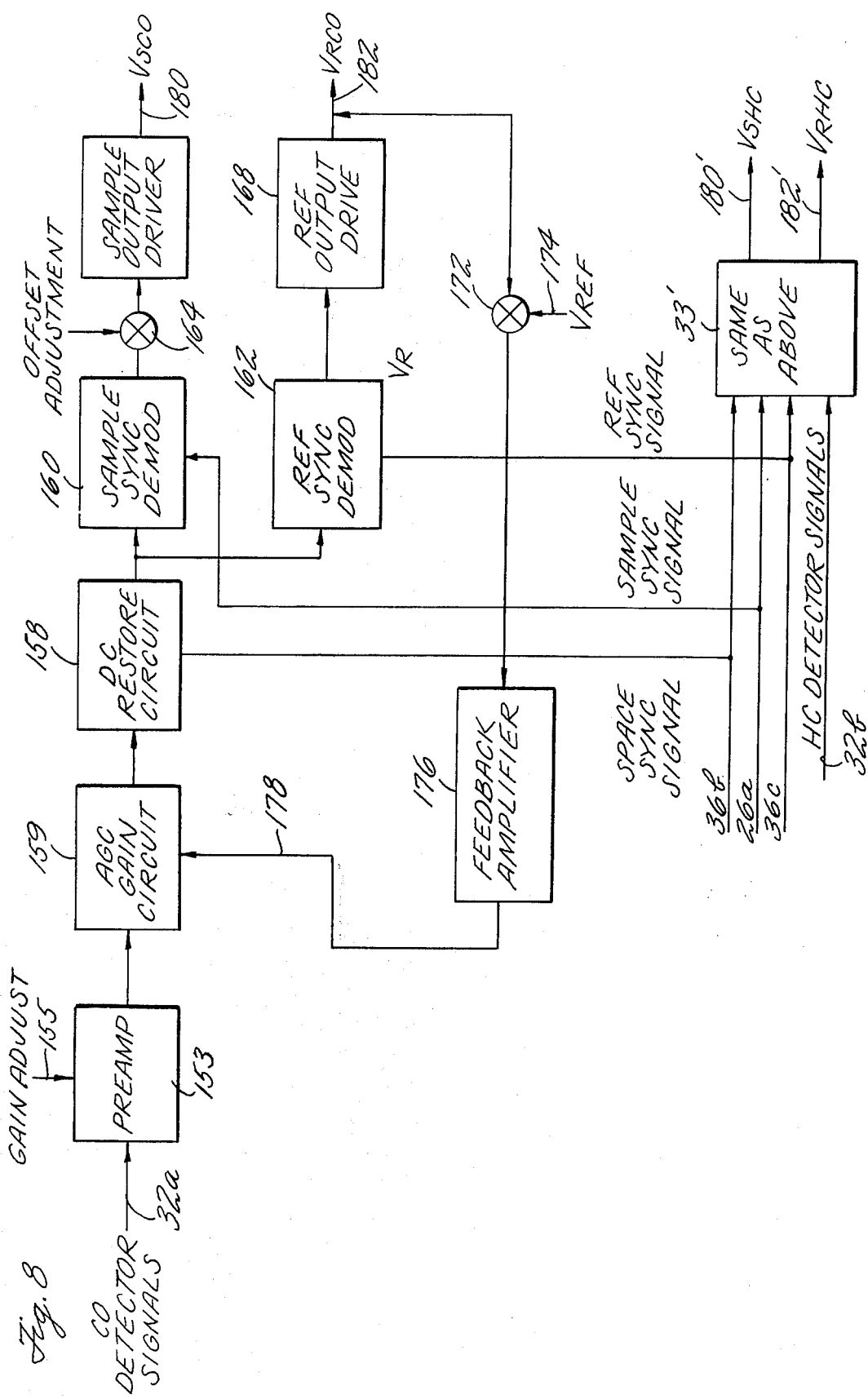

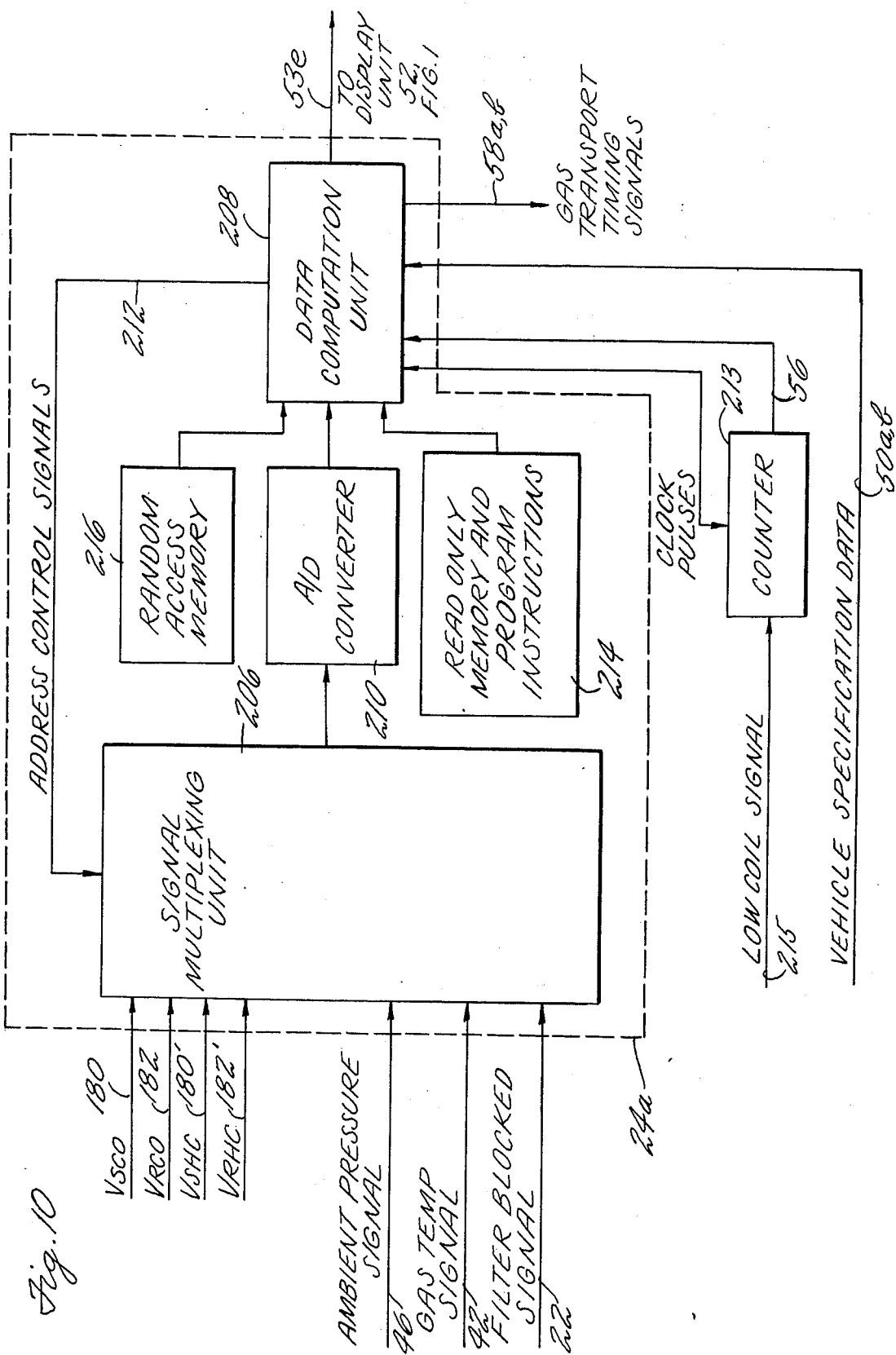

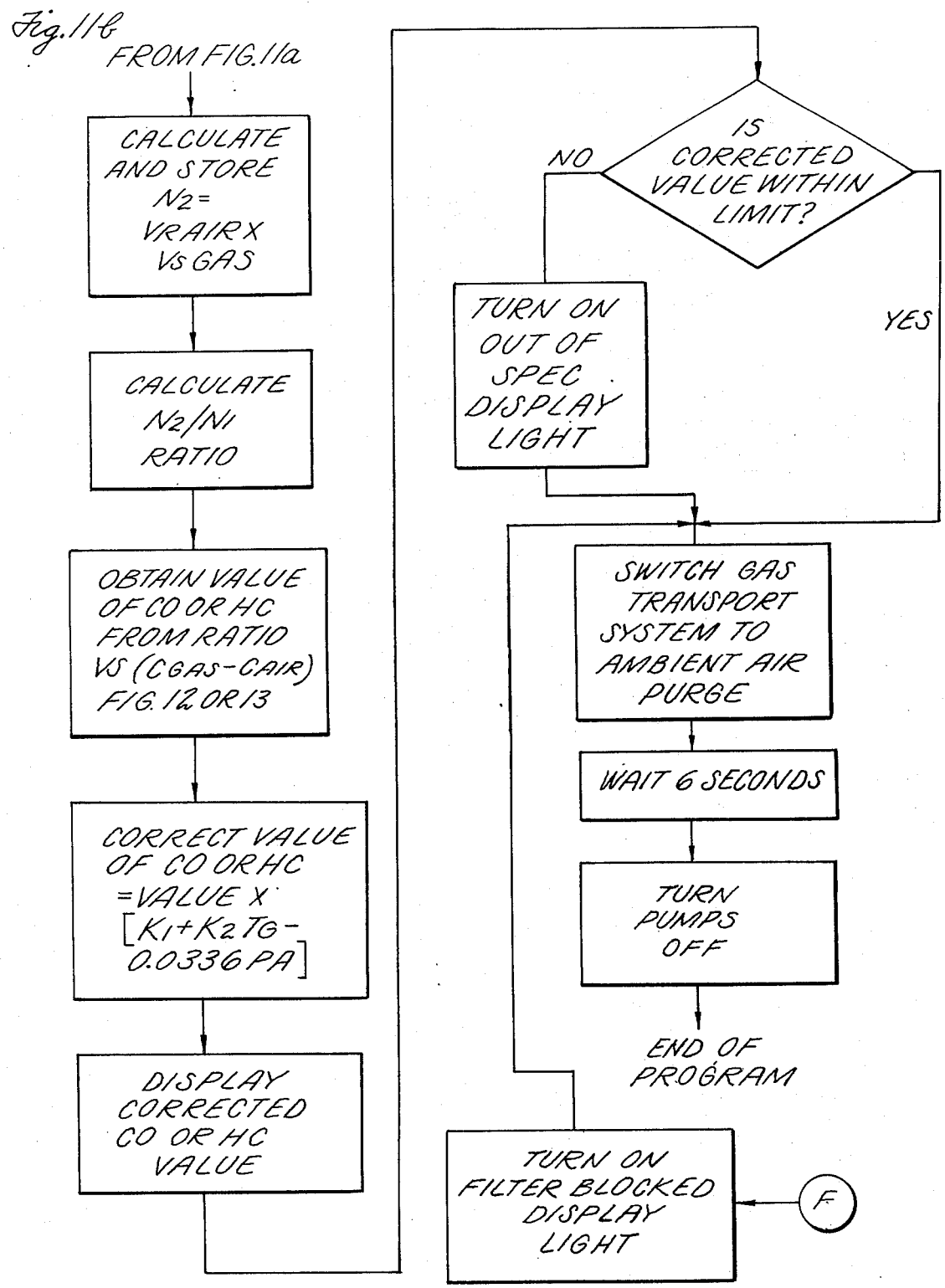

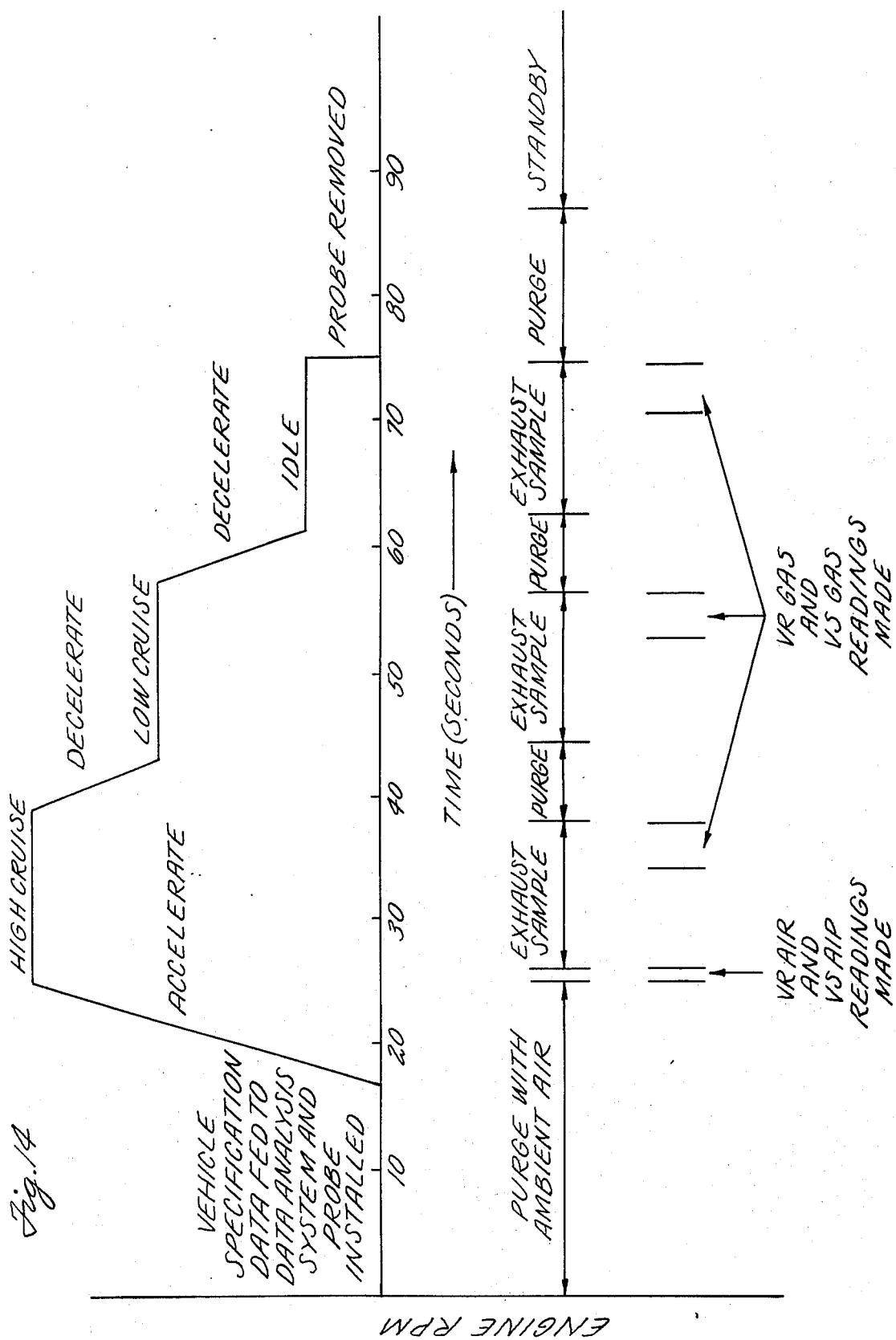

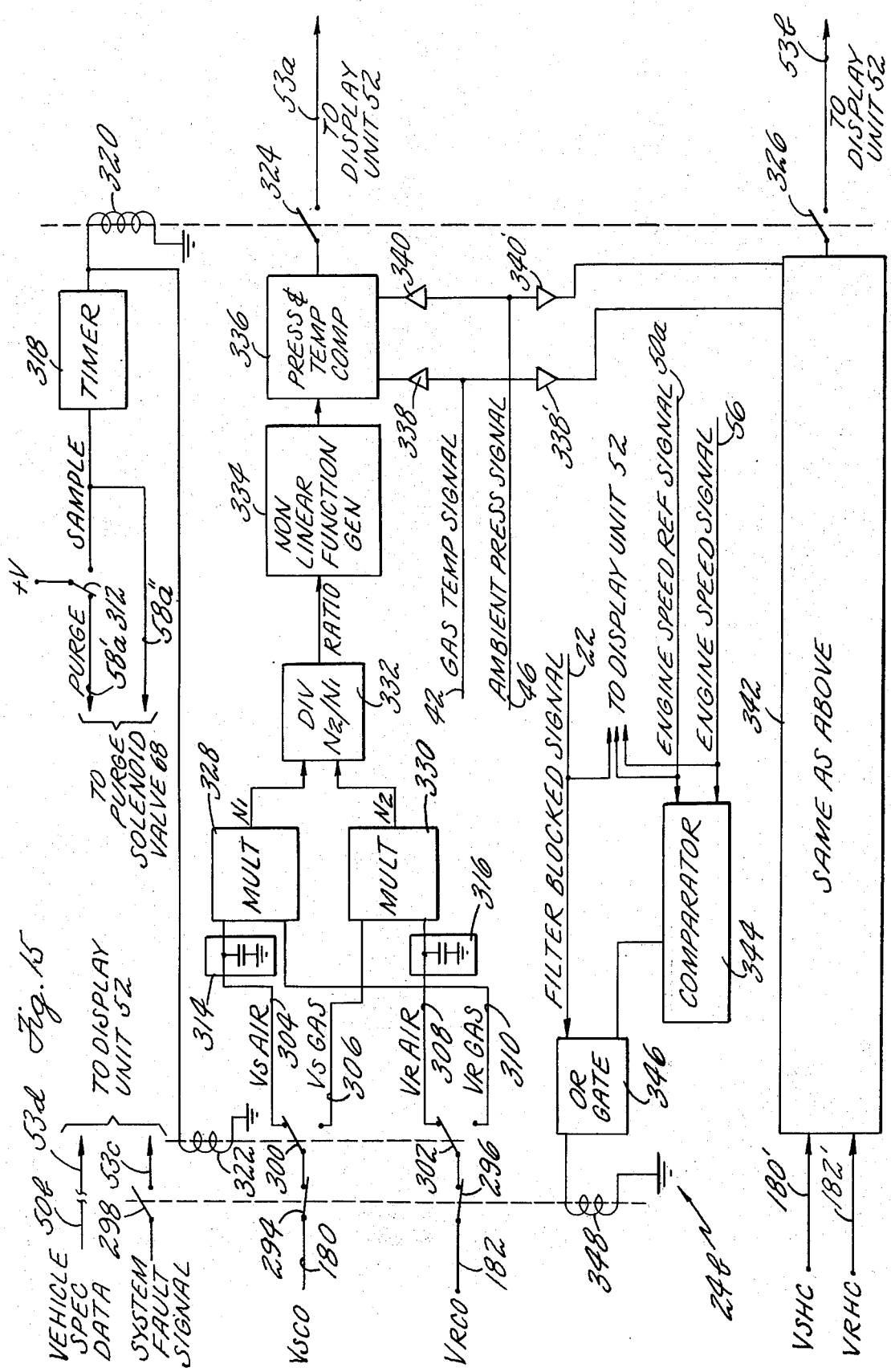

EXHAUST GAS ANALYZER HAVING PRESSURE AND TEMPERATURE COMPENSATION

BACKGROUND OF THE INVENTION

1. Field of the Invention

This invention relates to an exhaust gas analysis system for determining the concentration of selected contaminants in the exhaust gas emission from a motor vehicle, and particularly to an exhaust gas analysis system which is compensated for changes in ambient pressure and exhaust gas temperature. The concentration of specified components in the vehicle exhaust gas, such as CO and HC is measured by a nondispersive infrared gas analyzer whose output is automatically compensated, by either digital or analog techniques, to take into account changes in ambient pressure and changes in the temperature of the exhaust gas.

2. Description of the Prior Art

Becaue of the recent public concern with environmental pollution, particularly that caused by the contaminants in the exhaust gas from motor vehicles, a number of exhaust gas analysis systems have been developed to determine the concentration of the exhaust gas contaminants. Because of their inherent accuracy and reliability, many governmental agencies have specified that vehicle exhaust gas analysis systems contain nondispersive infrared gas analyzers as the component in the system which measures the concentration of the contaminants in the exhaust gas. However, such gas analyzer units are normally calibrated only by the manufacturer and do not take into account changes in ambient pressure at the location where the exhaust gas analysis takes place, or changes in the temperature of the exhaust gas from the vehicle under analysis.

SUMMARY OF THE INVENTION

The present invention overcomes the deficiencies in the prior art gas analysis systems and provides a vehicle exhaust gas analysis system which automatically compensates the exhaust gas measurements for changes in ambient pressure and exhaust gas temperature.

In accordance with a preferred embodiment of the invention, the electronic output signals from a nondispersive infrared gas analyzer are used to compute the amount of the selected contaminants in the exhaust gas. The computation takes place in either a digital or analog data analysis and control system. Signals indicative of ambient pressure and exhaust gas temperature are fed to the data analysis and control system and a correction is made to the computed measurements as a function of the ambient pressure and exhaust gas temperature.

In a digital embodiment of the present invention, the data analysis and control unit contains a digital computer and the corrections to the measurements for pressure and temperature are provided by digital means. In an analog embodiment of the present invention scaling amplifiers are used which produce a scaling signal in response to the ambient pressure and gas temperature signals, the scaling signals being used to compensate the output from the system.

BRIEF DESCRIPTION OF THE DRAWINGS

FIG. 2 is a schematic diagram of the gas transport system of FIG. 1.

FIG. 3 is a schematic diagram showing the details of the nondispersive infrared gas analyzer of FIG. 1.

FIG. 5 shows schematically the detector assembly of the infrared gas analyzer of FIG. 3.

FIG. 6 is a perspective view of the infrared source in the infrared gas analyzer of FIG. 3.

FIG. 7 is a graph showing the detector and synchronization output signals produced by the infrared gas analyzer of FIG. 3.

FIG. 8 is a schematic block diagram of the signal processing electronics of FIG. 1.

FIG. 9 is a simplified schematic block diagram of the signal processing electronics of FIG. 1 showing the gains of the signal amplifiers.

FIG. 10 is a schematic block diagram of a digital embodiment of the data analysis and control system of FIG. 1.

FIG. 14 is a chart showing the timing of the ambient air purge, exhaust gas sample and detector output readings as a function of vehicle engine speed.

FIG. 15 is a schematic diagram of an analog implementation of the data analysis and control system of FIG. 1.

FIG. 16 is a graph showing the characteristics of the HC filter of FIG. 5.

FIG. 17 is a graph showing the characteristics of the CO filter of FIG. 5.

DESCRIPTION OF THE PREFERRED EMBODIMENT

Figure 1:
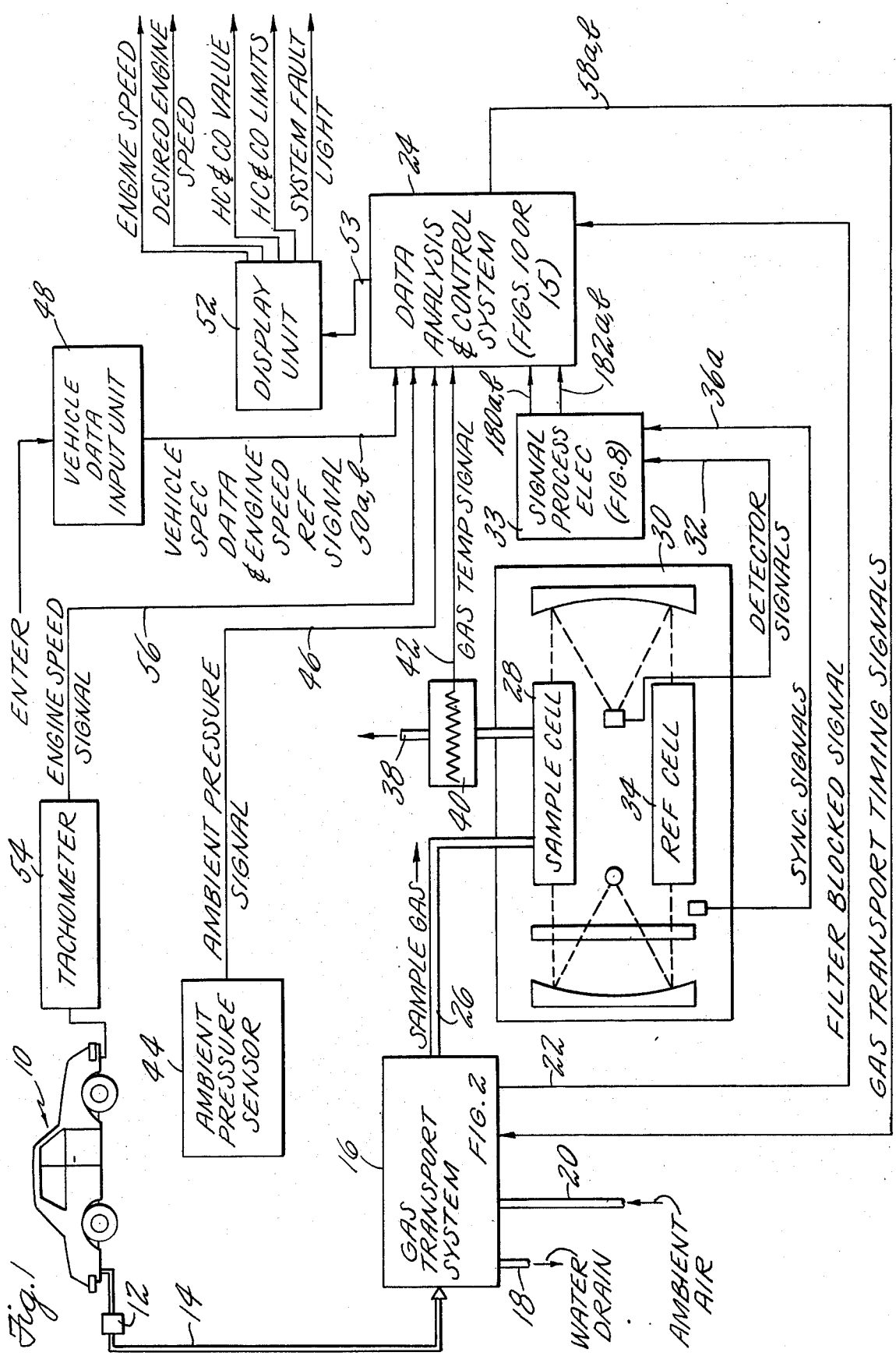
FIG. 1 is a schematic diagram partially in block diagram form of the vehicle exhaust gas analysis system connected to a vehicle and including an output display unit.

The basic vehicle exhaust gas analysis system is shown schematically in FIG. 1. A motor vehicle, shown as an automobile 10 and typically containing an internal combustion engine which emits exhaust gases containing pollutants, has attached to its exhaust emissions system, preferably at the tail pipe, an exhaust probe 12 which is designed so that it will not slip out of the vehicle's tail pipe under both normal vehicle vibrations and full load engine vibrations. A hand grip may be provided as part of the probe, and the probe should be flexible enough to extend into a curved tail pipe at least six inches if possible. For automobiles having dual exhausts two probes are required.

Attached to the probe 12 is a flexible gas transmission line which is preferably in the form of a hose 14 which serves as a link between the tail pipe probe 12 and a gas transport system 16. The hose 14 is preferably oil resistant and constructed of an internal hose material which will withstand high concentrations of gases without inducing hang up of the gases within the hose. Provisions may be made for storage of the hose 14 when not in use. The hose should also be able to withstand the abuse of being driven over by a heavy vehicle and return to its original shape and cross-sectional area within a short time. The hose 14 should be able to withstand tail pipe gas temperatures up to 200°F and have an inside diameter such as to permit purging of its entire length within a few seconds.

As is explained in detail in conjunction with FIG. 2, the gas transport system 16 contains replaceable particulate filters, a water removal system wherein water in the exhaust gas is eliminated through a water drain 18, a pumping system including a pump motor for pumping the gas to be analyzed to a nondispersive infrared gas analyzer, and a solenoid operated gas purge system which purges the system of exhaust gas and replaces it with ambient air from an inlet 20. The gas transport system 16 also contains a pressure switch, shown more particularly in conjunction with FIG. 2, which senses pressure to determine if a blockage has occurred in the gas transport system. A filter blocked signal is fed to a data analysis system 24 via a signal line 22 if a pressure loss in the gas transport system 16 is sensed.

The sample gas, either filtered exhaust emissions from the vehicle or ambient air, is fed from the gas transport system 16 through a gas line 26 into a sample cell 28, the sample cell being contained within a nondispersive infrared gas analyzer 30 which is described in detail in conjujction with FIGS. 3–6. Briefly, the nondispersive infrared gas analyzer 30 passes a beam of infrared radiation through the sample cell 28 into which the sample gas has been pumped. Two detectors, each having a separate light filter which blocks all but the wavelengths of interest, respond to the absorption of infrared radiation by the particular component of gas within the sample cell 28 which falls within the selected wavelengths passed by the filters, the electronic signals from the detector being fed via lines 32 into a signal processing electronics system 33, as described more particularly with respect to FIG. 8. The nondispersive infrared gas analyzer 30 also contains a reference cell 34 which is fully or partially sealed and which contains a reference gas, the infrared absorption of which is compared to that in the sample cell 28. Synchronization is provided by photosensitive devices which provide synchronizing signals via lines 36 to the signal processing electronics 33. After processing, the electronic signals are fed from the signal processing electronics 33 to a data analysis system 24 via lines 180a, b and 182a, b.

After the sample gas has been analyzed in the nondispersive infrared gas analyzer 30, it is removed from the sample cell 28 through a vent 38. Positioned within the vent 38 is a thermistor 40 which measures the temperature of the exhaust gas from the sample cell 28 and provides a signal indicative of gas temperature via line 42 to the data analysis system 24.

Since the absorption of infrared light within the sample cell is affected not only by the temperature of the gas within the sample cell 28 but by the ambient pressure, an ambient pressure sensor 44, which may be a simple pressure transucer, produces an ambient pressure signal which is fed to the data analysis sytem 24 via a signal line 46.

A particular feature of the present invention is that the concentration of more than one gas component may be measured simultaneously in the nondispersive infrared gas analyzer 30 by positioning a plurality of detectors with appropriate filters in the path of the infrared beam which has passed through the sample cell 28 and the reference cell 34. Typical contaminants specified by federal and state regulations at this time are carbon monoxide (CO) and a hydrocarbon component (HC), typically hexane. Regulations also specify various limits in the amount of CO and HC in the vehicle exhaust gases at various engine speeds and under specified load conditions. The present system is adapted to measure and display the amount of the selected emission contaminants in the vehicle exhaust gas under any of a number of specified test conditions. In a typical gas emission testing installation, the system operator will determine from the type of vehicle under test the particular test conditions which may be specified by local law, and the limits for CO, HC and/or other contaminants which may be specified by law. In a typical installation the operator will determine the appropriate vehicle specification data from tables (including speed and load conditions and HC and CO limits) and enter the data into a vehicle data input unit 48 which provides appropriate signals as to the specific vehicle data to the data analysis system 24 via lines 50. In more sophisticated systems which may include automotive diagnostic systems, the appropriate vehicle specification data may be stored in a memory unit and the operator merely enters the appropriate vehicle identification code into the vehicle specification data input unit 48, the appropriate vehicle specification data being automatically supplied to the data analysis system 24. Although not shown, the vehicle specification data on lines 50 may also be fed directly to a display unit 52 for display, preferably in digital form, for use by the operator.

The display unit 52 recieves data from the data analysis system 24 via lines 53. The display unit 52 may be a hand held controller which is used by the operator during the emissions testing, the hand held controller being of the type disclosed and claimed in a commonly owned, copending application of Mace Bell, Ser. No. 534,335 filed on even date herewith Dec. 19, 1974 and entitled VEHICLE DIAGNOSTIC HAND CONTROL. The display unit 52 may, either automatically or under the control of the operator, display any of the information which may be useful for conducting the emissions analysis testing. For example, the display unit may display the desired engine speed for the emissions test. At this time the operator causes the vehicle 10 to achieve the desired engine speed such as by depressing the vehicle accelerator pedal. A tachometer 54 may be connected to the vehicle 10 in a known manner to produce a signal indicative of engine speed, which is fed via a line 56 to the data analysis system 24 and which also may be displayed by the display unit 52. Although not shown, a dynamometer may be used to provide appropriate loading to the drive wheels of the vehicle, a signal indicative of vehicle load also being fed to the data analysis system 24. With desired engine speed and actual engine speed being displayed to the operator by display unit 52, the operator has a positive indication when the engine speed achieves the desired engine test speed. Once the vehicle has achieved the desired test speed for a sufficient time for the sample cell 28 to contain a representative exhaust gas sample, the emissions analysis may be performed and the measured CO and HC values displayed by display unit 52. The display unit 52 may also display, either automatically or at the request of the operator, the CO and HC limits so that it can easily be determined whether or not the vehicle meets the standards. The display unit 52 may also contain one or more indicator lights which automatically indicate a system fault, such as a blockage in the gas transport system 16 or a deviation from the desired engine speed.

The data analysis system 24 may be an analog processor, but preferably is a suitably programmed multipurpose digital computer of the type well known to those skilled in the art. The function of the data analysis system 24 is to compute the CO and HC values in a manner to be described from the various input data, to control the operation and timing of the gas transport system 16 by means of gas transport timing signals fed via lines 58a, b and to feed the desired data to display unit 52 via line 53. Examples of both analog and digital units for performing the desired functions will be described subsequently, the digital unit being shown in FIG. 10 and the analog unit in FIG. 15.

FIG. 2 shows in detail the gas transport system 16 of FIG. 1. The exhaust gas from the vehicle under test is fed through the tail pipe probe 12 and the hose 14 into a filtering system which consists of a coarse filter and water separator 60. The filter 60 is typically a 25 micron filter. Any water in the exhaust gas is separated out and fed from the filter 60 through a drain line 62 which contains a pump 64, the separated water ultimately being drained from the system via an outlet 18. After coarse filtration, the exhaust gas proceeds from the filter 60 to a fine filter 66 which is typically a 0.6 micron filter. Upon exiting from the fine filter 66, the filtered exhaust gas passes through a purge solenoid valve 68, and then through a pump 70 where the gas pases from the exhaust gas transport system 16 via the line 26 into the sample cell 28, which is contained within the nondispersive infrared gas analyzer 30.

Connected in the line between the fine filter 66 and the purge solenoid valve 68 is a pressure sensitive switch 74 which measures the adequacy of gas flow through the filters 60 and 66 by sensing the pressure drop across the filters via line 72. The pressure switch is referenced to ambient air and is typically set to close and produce a filter blocked signal via line 22 when the pressure drop across the filters increases to between 6 and 8 inches of mercury. Typically, a reduced pressure on line 72 is indicative of blockage in the filters, but can also be caused by the twisting of or an obstruction in the tail pipe probe 12 or hose 14. In any case, the generation of a filter blocked signal on the line 22 and the display thereof by a display light in display unit 52 of FIG. 1 is indicative of some malfunction in the gas transport system requiring action by the operator. Cleaning or replacement of the filters 60 or 66 is a typical solution to an excessive pressure drop.

The purge solenoid valve 68 is a two-way valve which provides a gas input via the pump 70 to the sample cell 28. In one position, the solenoid valve permits passage therethrough of the exhaust gas from the vehicle under test. In the other position the purge solenoid valve 68 blocks the exhaust gas line and causes ambient air from the input gas line 20 to pass through a normally open valve 72, through the purge solenoid valve 68, and into the sample cell 28 via the pump 70. The position of the purge solenoid valve 68 is determined by the gas transport timing signal on the line 58a, which is provided by the data analysis system 24 of FIG. 1. As is described hereinafter, operation of the gas analysis system requires that the sample cell initially be purged and contain ambient air, at which time a measurement is taken, by infrared techniques, of the magnitude of the selected contaminants in the ambient air within the sample cell. After the ambient air reading has been taken, the purge solenoid valve 68 is actuated via a signal on the line 58a to block the ambient air input and to permit the exhaust gas from the vehicle under test to fill the sample cell 28, at which time another reading of the contaminants contained in the gas in the sample cell is taken. After this latter reading, the purge solenoid valve 68 is again actuated to shut off the exhaut gas and to admit ambient air to purge the sample cell 28. Exhaust gas is admitted to the sample cell 28 only for the time necessary to obtain the desired data and is then immediately purged, in order to prevent contamination of the sample cell 28 by the impurities in the exhaust gas.

The pump 64, which purges water from the coarse filter 60, and the pump 70, which pumps either the exhaust gas or ambient air into the sample cell 28, are both controlled by a single pump motor 74 which responds to the gas transport timing signals on the line 58b. The pump motor 74 may be turned off to conserve power between tests.

The flow rate of pump 64 should be sufficient to insure that the water extracted from the exhaust emissions during testing of a vehicle will not accumulate in the filter 60, but should be sufficiently less than the flow of pump 70 to insure that adequate exhaust gas will flow from the exhaust gas probe 12 into the sample cell 28. For most efficient operation, the flow rate of the pump 70 should be such as to insure that an adequate sample of exhaust gas from the vehicle under test fills the sample cell in a few seconds. The source of ambient air 20 should be located such as to assure that the ambient air admitted to the system is not contaminated by exhaust emissions.

For initial calibration of the exhaust emissions analysis system, and for calibration at selected intervals during operation, a sample gas, such as pure nitrogen or a gas containing known amounts of selected contaminants as provided by container 76, is connected to the purge solenoid 68 through normally closed valve 78. When it is desired to calibrate the system, valve 72 is closed and valve 78 is opened and the calibration gas in container 76 is pumped into the sample cell 28. Calibration is performed by adjusting the signal conditioning electronics 33 as is described hereinafter.

The heart of the exhaust emissions analysis system is the nondispersive infrared gas analyzer 30 and its associated components shown schematically in FIGS. 3–6. Briefly, a source of infrared radiation of the desired wavelength is passed alternately through the closed reference cell 34 containing a reference gas such as clean air, and then through the gas sample cell 28 which contains either ambient air or the exhaust gas from the vehicle. The infrared radiation, after passing either through the reference cell or the gas sample cell, is focused through a suitable infrared filter onto a detector which produces electrical signals which will vary as a function of the absorption of light in the desired wavelength band by the selected gas component contained in each of the cells. After conditioning by suitable electronics as described in conjunction with FIG. 8, the output signals from the detector are used to calculate the concentration of the selected gas component. By placing two or more detectors with suitable filters in the same infrared radiation path, the concentration of two or more gas components can be measured simultaneously with a single gas analyzer.

Referring particularly to FIG. 3, there is shown the nondispersive infrared gas analyzer 30 which includes an optical bench assembly suitably enclosed by a rigid, shock free casing 102. A source of infrared radiation 104 is suitably mounted in the center of the assembly so that its output is focused into a parallel beam by a concave mirror 106 mounted within the optical bench assembly. An infrared window 108 having a high transmissivity in the three to five micron wavelength band may be positioned in front of the infrared source 104 to shield it from stray air currents. The infrared source 104 is preferably mounted in a holding bracket and completely shielded from the optical bench and surrounding area except for the window area. The details of the infrared source 104 and window 108 are described in conjunction with FIG. 6.

An opaque, nonreflecting chopper disk 110 is positioned between the infrared source 104 and the mirror 106, the chopper disk 110 being rotated in front of the mirror 106 by a motor 112 at a suitable speed to provide a chopping frequency to the detectors of between 32 and 55 Hz. The chopper disk 110, which is shown in greater detail in FIG. 4, contains a slot 114 through which the infrared radiation reflected by the mirror 106 may pass, the slot 114 extending circumferentially about the disk for about 90°. As a result of the rotation of the chopper disk 110 in the direction shown by the arrow 157 in FIG. 4, a rotating beam of radiation is generated (the locus of the beam scribes a cylinder) which passes alternately through the gas sample reference cell 34 and the gas sample cell 28. The cells 28 and 34 are identical tubes and include infrared windows 120 mounted at each end thereof to completely seal the ends of the tubes. The infrared windows 120 are transparent to the infrared wave band of interest, generally between 3 and 5 microns. The reference cell 34 is fully or partially sealed and contains a reference gas which may be clean air, while the sample cell 28 has either ambient air or vehicle exhaust gas fed thereto through line 26, the gas being vented from the sample cell by a line 127 through the vent 38 (FIG. 1).

As the rotating infrared beam passes through the reference and sample cells, it is focused by a second concave mirror 126 onto a detector array 128 shown schematically in FIG. 3 and described in greater detail with respect to FIG. 5. The detector array 128 contains two infrared detectors 130, 132 mounted within the image of the infrared source formed by the mirrors 106, 126. The detectors 130, 132 are preferably lead selenide (PbSe) and are firmly attached to a mounting bracket 134 which effectively shields the detectors from stray radiation. The position of the mounting bracket may be adjustable to assist in aligning theoptical system. Also mounted on the bracket 134 in front of each detector 130, 132 respectively are infrared filters 136, 138 which effectively shield the sensing surface of the detectors. Electrical leads 32a and 32b are connected to the detectors 130 and 132 respectively to provide the detector output signals to the signal conditioning electronics 33.

For purposes of illustration, it is assumed that the filter 136 is chosen to pass a narrow band of radiation centered at 4.74 microns where the maximum concentration of CO occurs, so that detector 130 will generate alternately on signal line 32a two electrical signals proportional respectively to the CO content in the sample cell and the reference cell, and it is assumed that the filter 138 is chosen to pass a narrow band of light centered at 3.41 microns, at which wavelength the maximum concentration of the hydrocarbon hexane occurs, so that detector 132 will generate alternately on signal line 32b two electrical signals proportional respectively to the HC content in the sample cell and reference cell. Since the infrared radiation source appears to be rotating by virtue of the rotation of the disk 110, the infrared radiation passes alternately through the gas sample cell 28 and the reference cell 34, and both of the detectors 130 and 132 will be illuminated simultaneously with radiation which has passed through the gas sample 28 and then with radiation which has passed through the reference cell 34. Each of the two detectors thus produces two output signals separated in time, the detector signals being denoted $V_R$ for the detector output when the detector has been illuminated by the infrared radiation which has passed through the reference cell 34, and as $V_S$ for the output signal which is produced by the detector as a result of the infrared radiation which has passed through the gas sample cell. The detector signals from each detector are shown by waveform A of FIG. 7. Signal line 32a from detector 130 produces the $V_S$ and $V_R$ signals which are subsequently referred to as $V_{SCO}$ and $V_{RCO}$, while signals line 32b from detector 132 produces similar $V_S$ and $V_R$ signals which are referred to subsequently as $V_{SHC}$ and $V_{RHC}$. The detector signals from lines 32a and 32b are then fed to the conditioning electronics 33 of FIG. 1 which is described in conjunction with FIG. 8.

The detectors 130 and 132 are responsive only to the radiation from infrared source 104 which has passed through either the gas sample cell 28 or the reference cell 34, and will not respond to radiation from the infrared source 104 at other times due to a series of baffles, not shown, which prevent illumination of the detectors at times other than when the infrared beam passes through the cells.

In order for the signal conditioning electronics 33 and the data analysis system 24 to distinguish between the sample cell and reference cell signals $V_S$ and $V_R$ produced by both of the detectors 130 and 132 and which appear on signal lines 32a and 32b, synchronization is provided by three light emitting diodes, each having associated therewith a phototransistor, the actuation of each phototransistor by its associated light emitting diode being synchronized to the rotation of the chopper disk 110 (FIG. 4) by a notch 144 in the outer perimeter of the chopper disk 110. Three light emitting diodes shown in FIGS. 3 and 4 as 146, 148 and 150 are positioned on one side of the rotating chopper disk 110, and corresponding phototransistors 152, 154 and 156 are positioned on the opposite side of the chopper disk. Corresponding light emitting diodes and phototransistors are positioned directly opposite each other so that when the notch 144 in the chopper disk passes between the light emitting diode and its corresponding phototransistor, a signal is generated by the phototransistor. These signals are fed to the signal processing electronics 33 on signal lines 36a, 36b and 36c.

Figure 4:
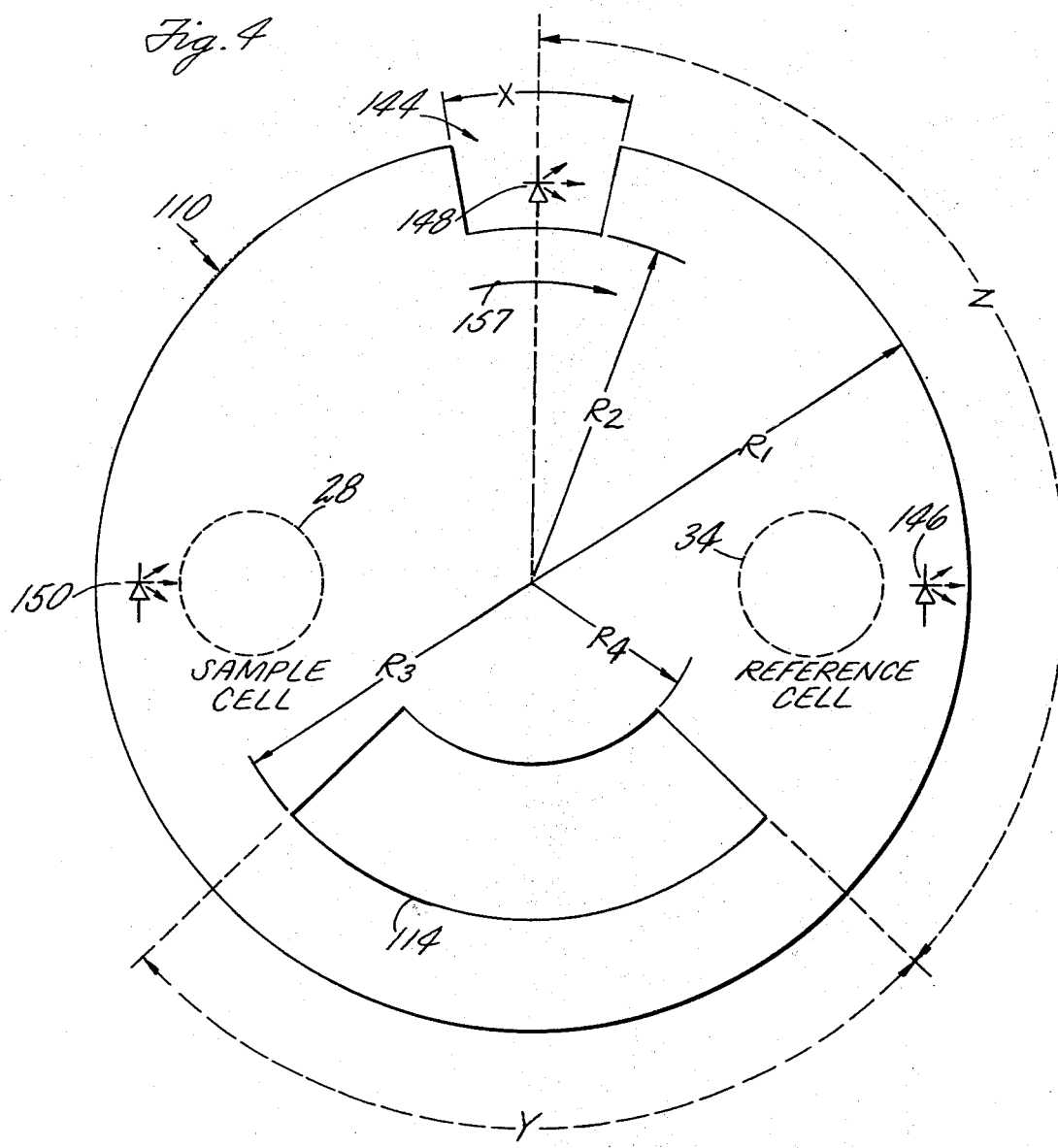
FIG. 4 is a view of the chopper disk used in the infrared gas analyzer of FIG. 3.

The positioning of the light emitting diodes relative to the chopper disk 110 and the sample and reference cells 28 and 34 is shown in FIG. 4. The sample light emitting diode 146 is 180° removed from the sample cell 28 so that when the slot 114 is positioned in line with the sample cell 28, the notch 144 will be positioned between the sample diode 146 and its associated phototransistor 152. At this time the sample sync signal shown at waveform B of FIG. 7 is generated by phototransistor 152.

As the chopper disk 110 rotates as shown by the arrow 157 in FIG. 4, the slot 114 will pass in front of the reference cell 34, and the notch 144 will pass between the reference light emitting diode 150 and phototransistor 156, which will produce the reference sync signal shown as waveform C in FIG. 7.

When the slot 114 of the chopper disk 110 is between the reference and sample cells (the position of the chopper disk shown in FIG. 4), the notch 144 will uncover the space light emitting diode 148. At this time the related phototransistor 154 will respond to the radiation from the light emitting diode 148 and will produce the space sync signal shown at waveform D in FIG. 7. The full revolution period of the chopper disk is between 18 and 31 milliseconds.

The sample and reference cells 28 and 34 are positioned in relationship to the three light emitting diode phototransistor pairs so that when the light emitting diode phototransistor pair 146 and 152 or 150–156 is at the midpoint of notch 144, the respective sample cell 28 or reference cell 34 is at the midpoint in the slot 114. The space sync diode 148 and its phototransistor 154 are 90° removed from the sample and reference diode phototransistor pairs. The light emitting diodes are arranged so that no signal from the diodes will significantly affect the output from the detectors 130 or 132.

Referring particularly to FIG. 4, the slot 144 preferably extends circumferentially an angle X which is a maximum of 21° and has a minimum angle equal to the response time of the signal conditioning electronics 33 for the rotational speed of the chopper disk. The notch 114 preferably covers an angle Y which is a minimum of 89° with a maximum angle such that the signal and reference cells 28 and 34 are covered, i.e., no light is transmitted therethrough, when the space sync signal is present from light emitting diode 148 and phototransistor 154 through notch 144 in the position shown in FIG. 4. The angle Z shown in FIG. 4 is selected so that the electrical signals from the detectors and the signal conditioning electronics are at their peak when the notch 144 produces the sample and reference sync signals by uncovering the sample and reference light emitting diodes 146 and 150.

As further shown in FIG. 4, the radius $R_2$ is preferably greater than radius $R_3$ by an amount sufficient to prevent illumination of the light emitting diodes from reaching the detectors by transmission or reflection. The magnitude of the radii $R_3$ minus $R_4$ is equal to or greater than the inside diameter of the sample and reference cells 28 and 34. The sample cell and reference cell are so positioned that when the center point of the cell is in the center of the slot 114, the entire cell diameter will receive and pass the infrared radiation. The radius $R_1$ is as large as possible to permit the slot 114 to be as large as possible in order to stabilize the readings from the detectors prior to gating of the synchronization signals by notch 144 as is explained in conjunction with FIG. 8. The light emitting diodes and phototransistor pairs are preferably located at a common radius from the center of the chopper disk 110.

The infrared source 104 of FIG. 3 and its window 108 are shown in greater detail in FIG. 6. The source 104 consists of a cartridge heating element 101 such as a Calrod unit which is inserted in a ceramic block 103, the block 103 being securely mounted to the optical bench. The ceramic block may be of the type known as Alsimag which is hollowed out to form a cavity into which the heating element 101 is positioned. The heating element 101 may be inserted into the cavity in the ceramic block 103 by drilling an appropriately sized hole shown at 105 through the ceramic block 103, and sliding the heating element 101 into the cavity therethrough. The heating element 101 may be secured within the ceramic block 103 by means of cement applied to the ends of the element 101 where it meets the ceramic block 103. With the construction as described the only contact between the element 101 and the ceramic block 103 is at the ends of the element 101. Since the ceramic block 103 has a low thermal conductivity, the element 101 is relatively unaffected by temperature changes which occur in the area surrounding the element.

The element 101 acts as a source of radiant energy when AC power is applied thereto such as through leads 109. To assure that the element 101 has a long lifetime before replacement is needed, the power applied thereto is slightly reduced. However, because the element produces a different temperature and hence a different energy distribution over its radiation spectrum as a function of applied power, sufficient power must be applied to assure the production of sufficient radiant energy in the band of interest, viz., between 3 and 5 microns.

The height of the opening in the ceramic block 103 through which the radiant energy from element 101 may pass is determined by the vertical height of the opening in mounting bracket 134 of FIG. 5, through which the detectors 130 and 132 are exposed to the radiant energy. It is preferred to maintain a 1:1 ratio between the height of the element 101 which radiates the infrared energy and the height of the detector opening through which the radiant energy is received.

Operation of the element 101 in the nondispersive infrared analyzer of FIG. 3 without a front shield may result in an instability in the output signals from the detectors. It was discovered that the temperature of the element 101 and consequently its energy level may be unstable, presumably because of drafts due to the rotation of chopper disk 110 only a few inches away. To solve this problem, a sapphire window 108 is positioned in front of the window in the ceramic block, the window 108 being transmissive to light in the 3–5 micron region. With the window 108 installed, the signal from the detectors is very stable.

Germanium or silicon windows would not be appropriate for the window 108 because of their variation with temperature. Sapphire is not affected in its transmission of radiation with temperature changes, and also has the ability to physically withstand extremes in temperature.

The sapphire window 108 is mounted in a stainless steel bracket 107, the bracket being L shaped and extending along the top of the ceramic block 103 where it is secured to the ceramic block by conventional hardware such as a screw 107a. Alternately the bracket 107 can be secured to the optical bench assembly to which the ceramic block 103 is also secured. The bracket 107 is relatively unaffected by heat, and maintains the sapphire window 108 in contact with the ceramic block 103 about the perimeter of the opening therein. The entire assembly 104 is substantially immune to temperature changes and provides a very stable infrared energy source.

Another advantage of the use of sapphire for the window 108 is that sapphire is transmissive to visible light, thereby permitting easy alignment of the optical bench assembly. Other window materials transmissive in the 3–5 micron region such as germanium and silicon are not transmissive to visible light.

The signal conditioning electronics 33 for the vehicle exhaust gas analysis system is shown schematically in FIG. 8. Two sets of signal conditioning electronics are required, one for the output signals from each of the detectors 130 and 132 which appear on lines 32a and 32b respectively. Only the signal conditioning electronics for detector 130 is shown in detail in FIG. 8, it being understood that identical signal conditioning electronics 33' is required for the signals from detector 132.

In FIG. 8, the electronic output signal from the detector 130 is fed via the signal line 32a into a preamplifier 153, the gain of which can be adjusted by a gain adjustment input 155 which may be by means of a potentiometer or the like. The output from the detector appearing on signal line 32a is an electronic signal of the type shown by waveform A of FIG. 7 having peaks $V_R$ and $V_S$ which correspond to the times during which the rotating infrared beam passes through the reference cell and sample cell, respectively. The amplitude of the detector signals in one embodiment may be generally between 7 and 25 millivolts, peak to peak.

After preamplification in amplifier 153 and noise filtering (not shown) the detector signals pass through an automatic gain control (AGC) circuit 159, the gain of the AGC circuit 159 being adjusted as explained hereinafter. It should be noted, however, that the gain of the AGC circuit 159 remains constant during each rotation of the chopper disk 110, that is, each combination of signals $V_S$ and $V_R$ during one rotation of disk 110 will have a constant gain applied thereto by circuit 159 for reasons described hereinafter.

The $V_S$ and $V_R$ signals leave the AGC circuit 159 with equal amplitudes above and below ground, as illustrated by the dotted line 161 in waveform A of FIG. 7. In order to reference the low edge of these signals to ground (as illustrated generally in waveform A), the amplified detector signals are fed to a DC restore circuit 158 where the DC level of the detector signals is referenced to ground. Another reason for the DC restore circuit 158 is that the infrared detectors, although shielded, receive continuous low level radiation from the infrared source and from the light emitting diodes in the optical bench assembly, and consequently this continuous background light applies an indeterminant, a steady state DC component to the detector output signals, causing drift from ground reference. The DC restore circuit 158 is synchronized with the space sync signal on the line 36b (as shown as waveform D of FIG. 7) to provide the fixed ground reference during the time of the space sync signal, to remove the constant DC bias component produced by the background light and to reference the low side absolutely to ground on a periodic basis.

After restoration, the detector signals are passed into a sample synchronous demodulator circuit 160 and into a reference synchronous demodulator circuit 162. The sample synchronous demodulator 160 is synchronized by the sample sync signal appearing on line 36a (shown in waveform B of FIG. 7) to provide a DC signal proportional to the sensed radiation and therefore proportional to the concentration of gas in the sample cell that absorbs radiation in the band of the filter. Consequently, only the radiation which has passed through the sample cell 28 (shown at waveform A of FIG. 7 as $V_S$) is then passed through an offset adjustment 164 and a sample output driver stage 166 to provide the output signal $V_{SCO}$ on a line 180.

The output from the DC restore circuit 158 is also fed to the reference synchronous demodulator 162 which is synchronized by the reference sync signal appearing on the line 36c (shown as waveform C of FIG. 7). Due to the synchronization, only the portion of the detector signal shown as $V_R$ in waveform A of FIG. 7 is demodulated in demodulator 162. The output of the reference synchronous demodulator 162 is a DC signal proportional to the concentration of CO (and other radiation absorbing gas) which is contained in the reference cell and which absorbs radiation of the band of the filter. The demodulated $V_R$ signal is fed to the reference output driver 168. The output from the reference output driver 168 is the output signal $V_{RCO}$ on a signal line 182.

In order to maintain the reference output signal $V_{RCO}$ on line 182 at a fixed voltage level so that both the output signals $V_{RCO}$ and $V_{SCO}$ will be compatible with the digital or analog data analysis system 24a or 24b to be described subsequently, an automatic gain control feedback is applied to the reference signal $V_{RCO}$. The reference signal $V_{RCO}$ is fed back via line 170 to a comparator 172 to which a constant reference signal $V_{REF}$ is also applied via a line 174. Any difference between the reference signal $V_{RCO}$ and the constant reference signal $V_{REF}$ will appear as an error signal which passes through feedback amplifier 176 and then via line 178 to the AGC circuit 159. The gain of the AGC circuit 159 is changed as a result of the feedback circuit to maintain the reference signal $V_{RCO}$ at a constant value, somewhere slightly above 8 volts. It will be apparent by reference to the waveforms shown in FIG. 7 that since the gain of the AGC circuit 159 is changed if at all only when a reference signal $V_{RCO}$ appears, and cannot be changed again until the next appearance of a reference signal $V_{RCO}$, the gain of the AGC circuit 159 will remain constant for the subsequent sample signal $V_{SCO}$ which passes through the AGC circuit 159. In other words, once the gain of the AGC circuit 159 is changed, it will remain constant for each pair of reference and sample detector signals.

Duplicate signal conditioning electronics 33' for the HC detector output signals on line 32b provides output signal $V_{SHC}$ on a line 180' and output signal $V_{RHC}$ on a line 182'.

FIG. 9 is a simplified block diagram which is equivalent to the signal conditioning electronics 32 shown in detail in FIG. 8. In FIG. 9 the gains applied by the various amplifiers of the signal conditioning electronics 33 to the detector output signals are shown within the blocks in order to assist with an understanding of the computations performed on the various signals by the data analysis system 24 of FIG. 1.

Referring to FIG. 9 the output from one of the detectors is shown on signal line 32a or 32b as signals $I_R$ and $I_S$ which appear alternately and are respectively the reference cell intensity equivalent detector output and the sample tube intensity equivalent detector output. The signals on lines 32a or 32b are fed to block 184 which contains a gain $K_P$ which is equivalent to the gain of preamplifier 153 of FIG. 8 as adjusted by the gain adjustment on line 155. The output from block 184 is fed to the block 186 which contains a gain $K_V$ which is equivalent to the automatic gain control gain shown at 159 of FIG. 8 and which is directly proportional to $K_F \times E$. The output from block 186 is then fed to switch 188 which represents the synchronous demodulators 160 and 162 of FIG. 7. No gain is applied to the signals by switch 188. The $V_S$ output from switch 188 is then fed to block 190 which produces a gain equal to $K_S$ which is the sample signal output amplifier gain as varied by the offset adjustment 164 of FIG. 7. A gain of unity is applied to the $V_R$ output from switch 188. The $V_R$ reference output voltage is then fed back to comparator 192 where it is compared to the $V_{REF}$ reference voltage, the comparator generating an error signal E which is equivalent to the difference between $V_R$ and $V_{REF}$. The error signal E is fed to block 194 where the gain $K_F$ of the feedback amplifier (176, FIG. 7) is applied thereto, and the output from block 194 is fed to block 186 to vary the gain $K_V$ therein in accordance with the output from block 194, and which is proportional to $K_V \times E$.

If the gas sample cell 28 is filled initially with ambient air, and the infrared radiation beam is rotated and passed through both the sample cell 28 and the reference cell 34 while ambient air is contained in the gas sample cell, the reference output voltage $V_R$ and the sample output voltage $V_S$ at that time can be represented as $V_{R\ AIR}$ and $V_{S\ AIR}$. If the purge solenoid 68 of FIG. 2 is then actuated to block the ambient air input and admit exhaust emissions from the vehicle under test into the sample cell 28, and if the rotating infrared radiation beam is then passed through the reference and sample cells while the sample cell is filled with exhaust gas, the reference output voltage and sample output voltage at that time can be represented as $V_{R\ GAS}$ and $V_{S\ GAS}$. It will be shown that by using the data analysis system 24 (FIG. 1) to perform the calculation:

Equation 1:

$$\frac{V_{R\ AIR}}{V_{R\ GAS}} \times \frac{V_{S\ GAS}}{V_{S\ AIR}} = \text{RATIO},$$

there is produced a ratio which is equivalent to the amount of a particular contaminant, CO or HC, in the emission gas with respect to the amount of the particular contaminant in the surrounding atmosphere and contained in the ambient air initially admitted into sample tube 28. If, instead of ambient air, the sample tube is initially filled with a reference gas which contains zero concentration of the particular contaminant gas, the ratio shown by Equation 1 will be an absolute ratio of the amount of the particular contaminant to a sample which contains none of the contaminant.

By performing the computation shown in Equation 1 such as by a digital computer programmed in accordance with techniques known to those skilled in the art, or by performing the calculation in an analog manner, the amount of the particular contaminant is uniquely measured. The ratio calculated by Equation 1 is then compensated for nonlinearities in the gas sampling and measurement system, and is then further corrected for changes in ambient pressure and gas temperature. The compensated ratio is then fed to the display unit 52 of FIG. 1 and is equivalent to the percentage of CO in the exhaust gas or the parts per million of HC in the exhaust gas.

FIG. 10 shows a preferred embodiment of the emissions analysis system in which the computations and corrections are performed by a digital data analysis system 24a which includes a digital data computation unit 208. The digital computation unit 208 may be a general purpose digital computer. A flow chart illustrating representative program steps performed by the digital data computation unit 208 is described in FIG. 11.

FIG. 10 contains a signal multiplexing unit 206. Feeding into the signal multiplexing unit 206 are the output signals $V_{SCO}$, $V_{RCO}$, $V_{SHC}$ and $V_{RHC}$ from the signal conditioning electronics 133 and 133' of FIG. 8 on lines 180, 182, 180' and 182', respectively. Also fed into the signal multiplexing unit 206 are the filter blocked signal on the signal line 22, the gas temperature signal on the signal line 42, and the ambient pressure signal on the signal line 46.

The signal multiplexing unit 206 receives each of the analog input signals and feeds the selected signal at the proper time to data computation unit 208 through an analog-to-digital converter 210 under the control of the address control signals appearing on line 212.

Also fed directly to the data computation unit 208 are the vehicle specification data signals on lines 50a,b and the engine speed signal on signal line 56. The engine speed signal may be generated as shown in FIG. 1 by means of a tachometer, or a counter 213 may be used as shown in FIG. 10 to generate a signal on line 56 which is proportional to engine speed. Fed to the counter 213 are clock pulses from a source, not shown within data computation unit 208, and a series of timing pulses from the low coil of the vehicle under test on a line 215. The counter 213 is adapted to be actuated by a selected low coil pulse, and stopped by the next low coil pulse, the number of clock pulses counted therein between coil pulses being proportional to engine speed. For example, if the vehicle under test has an 8 cylinder engine, the time between two low coil pulses is equal to ¼ revolution of the engine, or 90°. The data computation unit 208 receives the count from counter 213 on line 56 and computes the engine speed therefrom, the computation being a function of the number of engine cylinders, which data has been fed to the data computation unit via lines 50a,b with the vehicle specification data.

The data computation unit 208 as previously indicated may be a general purpose digital computer. The program instructions and necessary additional data such as constants are stored in a read only memory 214 which controls the operation of the data computation unit 208. Temporary storage during computation is provided by a random access memory 216 which is in communication with the data computation unit 208. The outputs from the data computation unit 208 include an input to the display unit 52 via output line 53e and the generation of gas transport timing signals on signal lines 58a,b, the latter signals being fed to the exhaust gas transport system 16 described in detail in FIG. 2 and which signals control the actuation of the purge solenoid valve 68 and the actuation of pump motor 74 to cause either ambient air or exhaust gas to fill the sample tube 28 at the proper times.

Figure 11A:
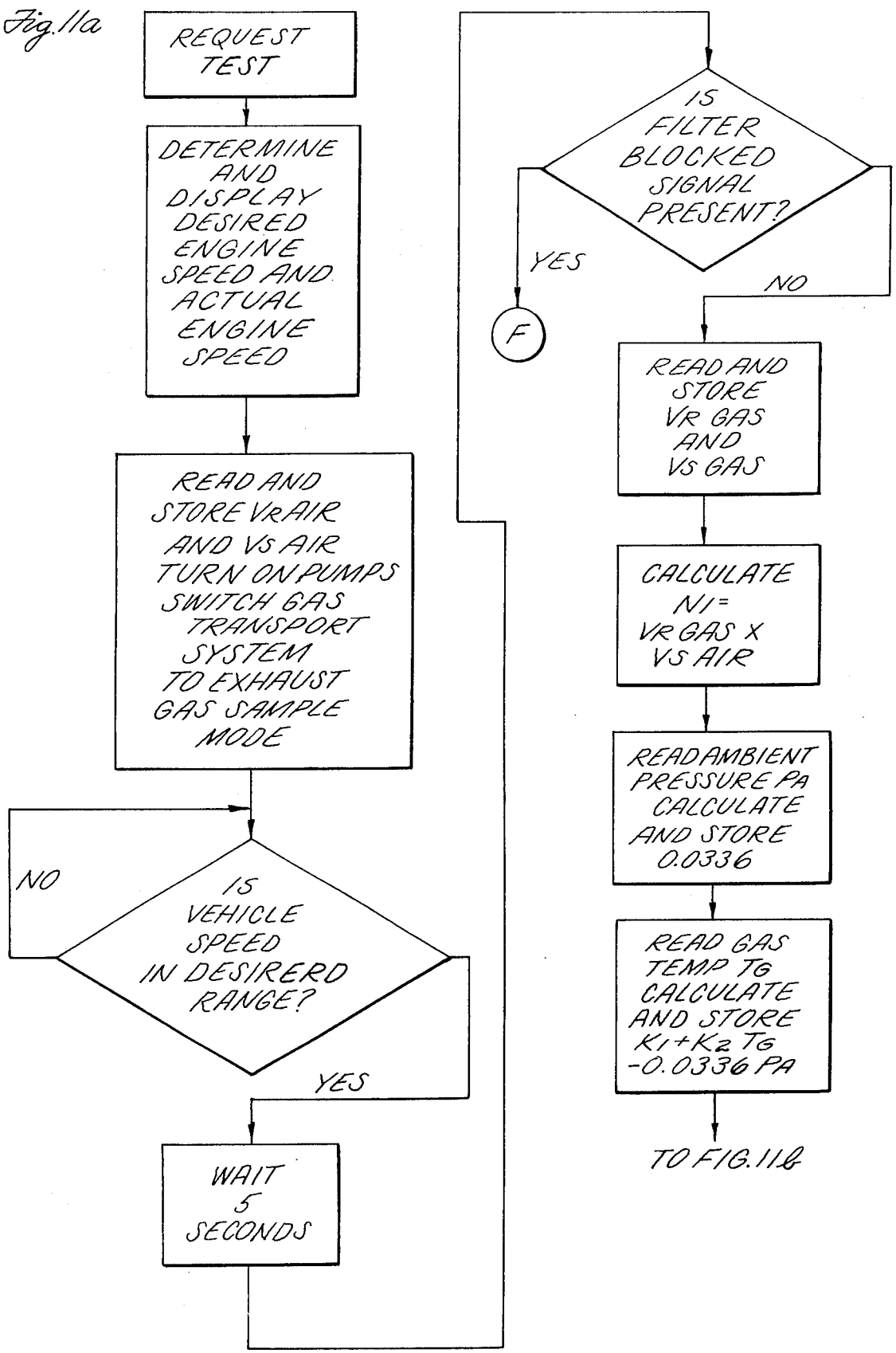
FIG. 11 is a flow chart of the program instructions for the digital computation unit of FIG. 10.

The data computation unit 208 of FIG. 10 accepts the signals from the signal multiplexing unit 206, performs the computation shown by Equation 1 in a manner such as is shown by the flow chart in FIG. 11, and corrects the calculated ratio for nonlinearities, and for ambient pressure and gas temperature.

Equation 1 is derived as follows. According to the Beer-Lambert Law:

Equation 2:

$$I_v = I_{v_0} e^{-\sigma(v)cl}$$

where $I_v$ = intensity of light at frequency $v$ after transmission through the gas $I_{v_0}$ = initial light intensity $\sigma_v$ = absorption coefficient of the gas at frequency $v$ C = concentration of the gas by volume l = path length through the absorbing gas.

$\sigma_v$ is a function of pressure and temperature as well as frequency.

While the filters 136 and 138 which shields the detectors 130 and 132 have a finite band spread and do not absorb completely at one wavelength, Equation 2 is sufficiently accurate when a high quality filter is used to determine a mean absorption coefficient $\sigma_v$. Since air is composed almost entirely of diatomic gases, oxygen and nitrogen, which do not absorb infrared radiation, if a radiation beam of fixed intensity is measured at the 4.74 micron (CO) and 3.41 (HC) micron bands after being passed through a sample tube containing first ambient air and then a vehicle emission gas, the concentration of CO and HC in the gas can be computed from the change in signals. The c and l terms in Equation 2 may be determined by calibration with the sample tube filled with a calibration gas having a known concentration of the gases.

For purposes of deriving Equation 1 and showing its relationship to Equation 2 it can be seen from FIG. 9 that Equation 3:

$$V_R = I_R \times K_P \times K_V$$

and $$V_S = I_R \times K_P \times K_V \times K_S.$$

Since one of the unique features of the present invention is the avoidance of the need to manually correct for changes in span (range of gross input signal magnitude) and zero settings, four measurements are made. The reference and sample voltages $V_R$ and $V_S$ are made with ambient air in the sample tube, and at a later time the reference and sample voltages $V_R$ and $V_S$ are made with the exhaust gas in the sample tube. Consequently Equations 1 and 3 can be combined into Equation 4 as shown below:

Equation 4:

$$\frac{V_{R\,AIR}}{V_{R\,GAS}} \times \frac{V_{S\,GAS}}{V_{S\,AIR}} = \frac{(I_R \cdot K_P \cdot K_V)_{AIR}}{(I_R \cdot K_P \cdot K_V)_{GAS}} \times \frac{(I_S \cdot K_P \cdot K_V \cdot K_S)_{GAS}}{(I_S \cdot K_P \cdot K_V \cdot K_S)_{AIR}}$$

$K_P$ and $K_V$ are independent of whether emission gas or ambient air are in the sample tube and will change only with time. Since the sample and reference measurements are made almost simultaneously, terms may be cancelled out as shown below in Equation 5:

Equation 5:

$$\frac{V_{R\,AIR}}{V_{R\,GAS}} \times \frac{V_{S\,GAS}}{V_{S\,AIR}} = \frac{I_{R\,AIR}}{I_{R\,GAS}} \times \frac{I_{S\,GAS}}{I_{S\,AIR}} \times \frac{K_{S\,GAS}}{K_{S\,AIR}}$$

If the gain $K_S$ shown in block 190 of FIG. 9 is a simple electronic circuit with near zero drift, and if the measurements with ambient air and exhaust gas in the sample tube are taken relatively close together in time, $K_S$ may also be cancelled out, leaving Equation 6:

Equation 6:

$$\frac{V_{R\,AIR}}{V_{R\,GAS}} \times \frac{V_{S\,GAS}}{V_{S\,AIR}} = \frac{I_{R\,AIR}}{I_{R\,GAS}} \times \frac{I_{S\,GAS}}{I_{S\,AIR}}$$

The Beer-Lambert Law of Equation 2 may now be used to rewrite Equation 6 in terms of initial source intensity as shown below in Equation 7:

Equation 7:

$$\frac{V_{R\,AIR}}{V_{R\,GAS}} \times \frac{V_{S\,GAS}}{V_{S\,AIR}} = \frac{I_{Re} \cdot olc(AIR)}{I_{Re} \cdot olc(GAS)} \times \frac{I_{Se} \cdot olc(GAS)}{I_{Se} \cdot olc(AIR)}.$$

Since a reference gas such as clean air is always contained in the reference cell 34, Equation 7 converts into Equation 8 as shown below:

Equation 8:

$$\frac{V_{R\,AIR}}{V_{R\,GAS}} \times \frac{V_{S\,GAS}}{V_{S\,AIR}} = \frac{I_{Re} \cdot olc(AIR)}{I_{Re} \cdot olc(GAS)} \times \frac{I_{Se} \cdot olc(GAS)}{I_{Se} \cdot olc(AIR)}$$

which simplifies to

Equation 9:

$$\frac{V_{R\,AIR}}{V_{R\,GAS}} \times \frac{V_{S\,GAS}}{V_{S\,AIR}} = \frac{e^{-olc(GAS)}}{e^{-olc(AIR)}} = e^{-ol(C_{GAS} - C_{AIR})}$$

On the left-hand side of Equation 9 are only measured parameters and on the right-hand side are only the constants e, $\sigma$ and l and the desired quantities ($C_{GAS} - c_{AIR}$). No variables requiring zero or span adjustments remain.

The Equation 9 can be plotted as Equation 10 shown below:

Equation 10:

$$\frac{V_{R\,AIR}}{V_{R\,GAS}} \times \frac{V_{S\,GAS}}{V_{S\,AIR}} \text{ vs. } (C_{GAS} - c_{AIR})$$

Figure 12:
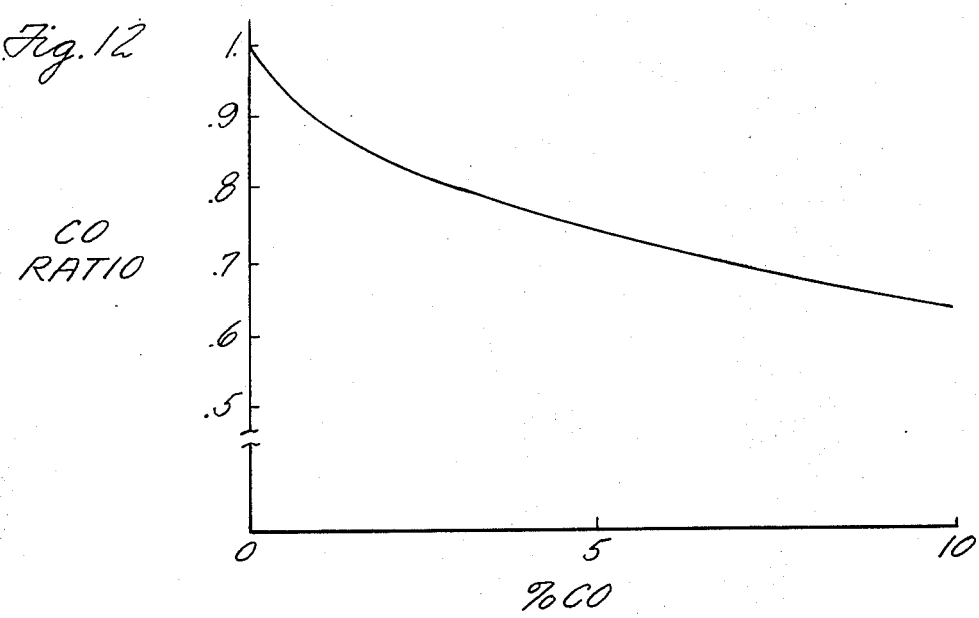
FIG. 12 is a plot of the CO percentage in the exhaust gas as a function of a computed CO ratio.
Figure 13:
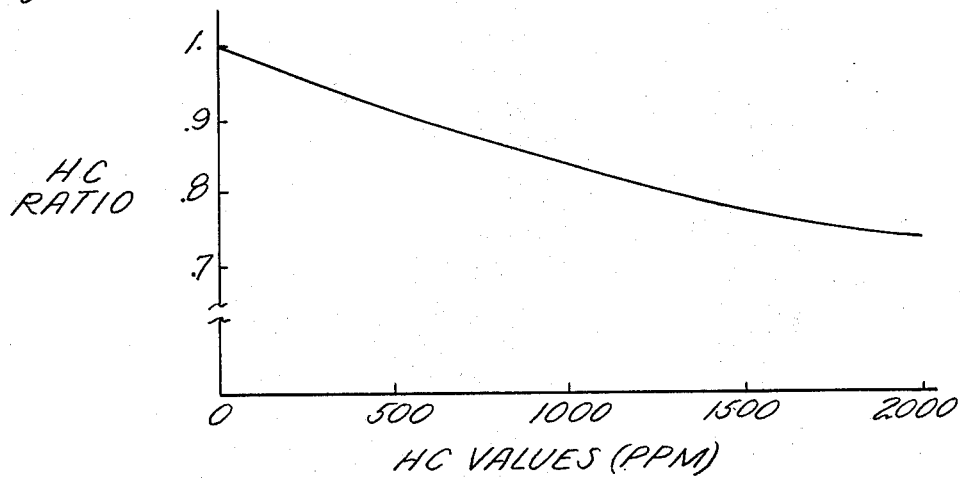
FIG. 13 is a plot of the HC content of the exhaust gas in parts per million as a function of a computed HC ratio.

Equation 10 is plotted from empirical data using known gas concentrations for CO in FIG. 12 and for HC in FIG. 13, which plots provide the basic calibration curve of the emissions analyzer. The curves are for a temperature of 30.0°C and a pressure of 29.75 inches of mercury. All individual systems produced in accordance with the invention are set to the same curve which is stored in the processor memory, block 214 of FIG. 10. In other words, by computing Equation 10 to produce a ratio signal indicative of the CO or HC ratio as shown initially in Equation 1, and by calibrating the computed ratio in accordance with the appropriate curve shown in FIG. 12 (CO) or FIG. 13 (HC), the calibrated ratio signal for CO is provided in percent concentration CO and the calibrated ratio signal for HC is provided in parts per million HC.

Since the value of $\sigma$ is actually affected by ambient pressure and gas temperature, these two parameters are measured and compensation is provided, using the computer program stored in random access memory 214 of FIG. 10. The pressure and temperature corrections for CO and HC are shown in Equation 11:

Equation 11:

CO = CO calibrated ratio (uncorrected) × [1.8256 + 0.0058 $T_G$ −0.0336 $P_A$]

HC = HC calibrated ratio (uncorrected) × [1.9336 + 0.0022 $T_G$ − 0.0336 $P_A$]

where $T_G$ = gas temperature (°C) of exhaust gas from thermistor 40 of FIG. 1, and PA = ambient pressure (mm Hg) from sensor 44 of FIG. 1.

Once the computed ratio has been calibrated according to the curves of FIGS. 12 or 13, and has been corrected for pressure and temperature in accordance with Equation 11, the resultant computations of CO and HC values from data computation unit 208 of FIG. 9 are sent to the display unit 52 where the percentage of CO and/or the amount of HC in parts per million is displayed in digital or numerical format for the operator. If desired, the CO and HC values can be compared with the limits for CO and HC contained as part of the vehicle specification data and a display light illuminated to indicate if the vehicle under test is out of specification for amounts of either CO, HC or both.

It is important that the measurements of $V_R$ and $V_S$ using ambient air in the sample cell and the measurements of $V_R$ and $V_S$ using exhaust gas in the sample cell be made reasonably close together in time in order to prevent changes in the radiation from the infrared source from changing the output from the detector.

FIG. 11 is a simplified flow chart showing representative program steps which may be contained in the program instructions stored in random access memory 214 of FIG. 10 and which control the computations in data computation unit 208 and the transmission of the input signals from the signal multiplexing unit 206 to the analog-to-digital converter 210 and then to the data computation unit 208. The outputs from the data computation unit 208 to the display unit 52 via line 53e and the initiation of the gas transport timing signals on lines 58a,b are also controlled by the program steps shown in FIG. 11. It will be apparent to one skilled in the art of digital computer programming that various other program steps and implementations of the invention may be performed depending on the specific construction and operation of the data computation unit 208.

Although not shown in the flow chart of FIG. 11, the engine speed may be continuously monitored, i.e., compared with the desired vehicle engine speed illustrated as the engine speed reference signal in conjunction with the vehicle specification data on lines 50a,b of FIG. 1. If the actual engine speed is out of the desired range, i.e., a range centered about the desired engine speed, the HC and CO values are not displayed in display unit 52 and an indicator light in display unit 52 may be turned on, indicating that the engine speed must be adjusted. The filter blocked signal on the line 22 may also be continuously monitored, and if present the computations terminated and the system purged with ambient air. The manner of implementation of these program steps may be in accordance with programming techniques which are well known to those skilled in the art and are therefore not described in detail.

If desired the $V_{R\ GAS}$ and $V_{S\ GAS}$ signals may be continuously monitored during the time that these readings are made, new $V_{R\ GAS}$ and $V_{S\ GAS}$ signals being taken approximately twice per second. The computations of the HC and CO values may also be continuously updated in like manner, and averaged on a continuous basis so that the values displayed in display unit 52 are the average values of HC and CO. Other changes in the program steps will be apparent to those skilled in the art.

FIG. 14 shows a typical timing chart for the emissions analysis of the exhaust gas from an automobile as performed by the system of FIG. 1 and the data analysis system 24a of FIG. 10. Once the vehicle is in proper position for the test, the operator actuates the gas analysis system and gas transport timing signals are fed from the data analysis system 24a via lines 58a,b to ensure that the sample cell is purged with ambient air. If the system has not been left purged with ambient air in an immediately preceding cycle, sufficient time is allowed so that it is assured that the sample cell is first filled with ambient air. At the same time the operator installs the probe 12 on the vehicle tail pipe and enters the vehicle specification data into the data analysis system 24a via lines 50a,b. Display unit 52 displays the desired engine speed as digital data which is read by the operator, and the operator then causes the vehicle to accelerate to the desired engine speed, in this example high cruise. The actual engine speed is fed to the data analysis system via line 56. Once the engine reaches the desired speed, and with the sample cell filled with ambient air, the $V_{R\ AIR}$ and $V_{S\ AIR}$ readings are taken and sent to the data analysis system for storage.

Once the $V_{R\ AIR}$ and $V_{S\ AIR}$ readings have been made, gas transport timing signals are fed from data analysis system 24a to the purge solenoid valve 68 of FIG. 2 to cause the solenoid valve to block the ambient air input to the sample cell and pump exhaust gas from probe 12 and hose 14 into the sample cell. After a time sufficient to assure that the sample cell is filled with exhaust gas, the $V_{R\ GAS}$ and $V_{S\ GAS}$ readings are taken.

It should be noted that during acceleration, raw fuel is fed into the engine, and any HC or CO content measurements made on the exhaust gas from the vehicle at this time will be very high and unreliable. The operator must wait until the excess fuel is burned and the emissions gas stabilizes before valid readings of CO and HC can be made. A time lapse of seven seconds is considered adequate after acceleration for reliable measurements to be made.

Once the desired readings are taken, the sample cell is again purged with ambient air to remove the exhaust gas, but no additional $V_{R\ AIR}$ or $V_{S\ AIR}$ readings are required. During the purge time the operator causes the vehicle to decelerate to a low cruise condition, the desired engine speed having been displayed in display unit 52 after the initial $V_{R\ GAS}$ and $V_{S\ GAS}$ readings were taken. After the ambient air purge, exhaust gases are again admitted to the sample cell and new $V_{R\ GAS}$ and $V_{S\ GAS}$ readings taken for the low cruise condition. The cycle of ambient air purge and exhaust gas sample is repeated for engine idle speed, and additional $V_{S\ GAS}$ and $V_{R\ GAS}$ readings taken for the idle condition. The system is then finally purged with ambient air and set in a standby mode, e.g., pump motor 74 of FIG. 2 may be turned off, until the next vehicle is in position and the cycle is repeated.

The ratio calculations may be made in the data computation unit 208 and displayed either during each purge-sample cycle, or when the cycle has been terminated. For the example given, three HC and CO ratio calculations will be made, one for each engine speed. Obviously the number of speeds at which measurements of emission contaminants are made can be varied.

It is important that the exhaust gas sample is fed into the sample cell for only the time required to obtain readings, the sample cell being purged with ambient air at all other times to prevent contamination of the cell by pollutants in the exhaust gas.

An analog implementation of the system of this invention is shown in FIG. 15. The various input signals in FIG. 1 are fed to an analog data analysis system 24b and which is equivalent to the digital data analysis system 24a of FIG. 10. Referring to the FIG. 15, the $V_{SCO}$ and $V_{RCO}$ signals appearing on signal lines 180 and 182 are fed respectively through normally closed switches 294 and 296, whose operation will be described subsequently, and then through switches 300 and 302 respectively, the $V_S$ signal being fed to lines 304 or 306 labeled $V_{S\ AIR}$ and $V_{S\ GAS}$ respectively depending on the position of switch 300, and the $V_R$ signal being fed to lines 308 or 310 which are labeled $V_{R\ AIR}$ and $V_{R\ GAS}$ respectively, depending on the position of switch 302. The position of switches 300 and 302 is determined by the position of switch 312 which is actuated manually by the operator of the system. Switch 312 has two positions, PURGE and SAMPLE, and is biased so that unless it is held by the operator in the SAMPLE position, it will return to the PURGE position. Switch 312 may be a time delay switch which returns to the PURGE position after a selected time such as eight seconds after being moved to the SAMPLE position. While in the PURGE position, a signal is fed via line 58 $a'$ to purge solenoid 68 to cause the purge solenoid to admit ambient air into the sample cell. While switch 312 is in the PURGE position, the switches 300 and 302 are normally biased as shown in FIG. 15, i.e., in contact with lines 304 and 308 respectively.

Assuming that switch 312 is in the PURGE position, the $V_{S\ AIR}$ signal on line 304 is fed to a sample and hold circuit 314 where the $V_{S\ AIR}$ signal is stored. Likewise the $V_{R\ AIR}$ signal on line 308 is fed to a sample and hold circuit 316 where it is stored.

When a vehicle is ready to be tested, and has reached the desired test speed as shown by an indication on the display unit 52, the operator moves switch 312 to the SAMPLE position. At this time a signal is fed via line 58$a''$ to the purge solenoid valve 68 to cause the ambient air inlet to be blocked and exhaust gas to be admitted to the sample cell 28. A timer 318 is also actuated, and after a suitable time such as seven seconds to assure that the sample tube is filled with exhaust gas, the timer 318 times out causing relays 320 and 322 to be actuated. Actuation of relay 320 closes normally open switches 324 and 326 whose operation will be described subsequently, and actuation of relay 322 moves switches 300 and 302 to feed the $V_{SCO}$ and $V_{RCO}$ signals on lines 180 and 182 to lines 306 and 310 respectively.

Connected to the output from sample and hold circuit 314 and also receiving the signal on line 308 is a multiplier 328 which generates the product $N_1 = V_{S\ AIR} \times V_{R\ GAS}$. Connected to the output from sample and hold circuit 316 and also receiving the signal on line 306 is a multiplier 330 which generates the product $N_2 = V_{S\ GAS} \times V_{R\ AIR}$. The $N_1$ and $N_2$ outputs from multipliers 328 and 330 are fed to a divider 332 where the division $N_2/N_1$ is effected. This division results in the RATIO of Equation 1. The RATIO signal from divider 332 is fed to a nonlinear function generator 334 where the compensation to the RATIO signal in accordance with the curve of FIG.12 is performed. Function generator 334 may be a simple diode network. The output from the nonlinear function generator 334 is then fed to pressure and temperature compensator 336 where the computed value of CO is compensated for pressure and temperature. To accomplish this compensation, the gas temperature signal on line 42 and the ambient pressure signal on line 46 are fed respectively through scaling amplifiers 338 and 340 into compensator 336, which provide the constants for $T_G$ and $P_A$ in Equation 11, which are then summed in a summing junction (in compensator 336) with a fixed signal representing the constant (1.8256) in Equation 11. The output of the summing junction is multiplied with the output of the function generator 334 in an analog multiplier (in the compensator 336).

The output from compensator 336 is the resultant CO measurement signal which is then fed through switch 324, now closed because of actuation of relay 320, and via line 53a to display unit 52. Once the CO measurement is made and displayed on display unit 52, the operator moves switch 312 back to PURGE, or switch 312 will move back to PURGE after a selected time delay, thereby opening switch 324 so that no signal can thereafter pass therethrough.

The HC measurements are made by analog apparatus 342 which is identical to that just described (except for the nonlinear function, which is that of FIG. 13) and which receives inputs $V_{SHC}$ via line 180' and $V_{RHC}$ via line 182', and also receives temperature and pressure input signals via scaling amplifiers 338' and 340'. The computed HC signal is fed via switch 326 and line 53b to display unit 52 at the same time that the CO signal is fed to the display unit.

If, during the measurements, the engine speed on line 56 deviates from the engine speed reference signal on line 50a by an amount determined within a comparator 344, or if a filter blocked signal appears on line 22, OR gate 346 is actuated and relay 348 is energized to open switches 294 and 296 so that a zero output signal is produced on lines 53a and 53b, and switch 298 is closed to cause a system fault signal to be passed to display unit 52 via line 53c.

Vehicle specification data in this embodiment which appears on line 50b may be fed directly to display unit 52 via line 53d.

FIGS. 16 and 17 show respectively the filter characteristics of the filters 138 and 136 of FIG. 5 which may be used to pass therethrough the specified wavelengths for measurement of HC and CO. The particular wavelengths chosen and described herein were selected by a governmental agency for emissions analysis testing. Since the components in automobile exhaust emissions of hexane and carbon monoxide occur at other wavelengths than those described, it is obvious that other wavelengths may be chosen to test for HC and CO components in the exhaust gas.

It will also be apparent to those skilled in the art that more than two detectors may be used in the system and that tests may be made for other contaminants such as carbon dioxide, acetylene, methane or nitrous oxide (NO), by simply replacing the filters with other filters which pass radiation at the desired wavelengths.

While the invention has been described with respect to preferred embodiments thereof, it will be apparent to those skilled in the art that changes and modifications may be made to the construction and arrangement of parts and the operation without departing from the scope of the invention as hereinafter claimed:

We claim:

1. A gas analysis system for measuring the amount of a selected contaminant in a sample gas comprising
   means for generating a beam of infrared radiation,
   a sample cell adapted to contain a gas,
   means for passing a sample gas through said sample cell,
   a reference cell containing a reference gas,
   means for passing said beam alternately through said sample cell and said reference cell,
   detector means responsive to said beam and producing respectively first and second electrical signals respectively indicative of the absorption of said beam by the selected contaminant within said cells,
   means responsive to said first and second signals for computing an output signal indicative of the amount of said selected gas contaminant in said sample gas,
   means for measuring the temperature of said sample gas and producing a gas temperature signal indicative thereof,
   means for producing a pressure signal indicative of the ambient pressure,
   and compensation means responsive to said gas temperature signal and said pressure signal for correcting said output signal.

2. A gas analysis system as in claim 1 in which said sample cell has an inlet port and an outlet port,
   said means for measuring the temperature of said sample gas including a thermistor located in the output port of said sample cell.

3. A gas analysis system as in claim 1 in which said means for producing a pressure signal comprises a pressure sensor responsive to ambient pressure.

4. A gas analysis system as in claim 1 in which said selected contaminant is carbon monoxide, and said compensation means includes means for multiplying said output signal by the relationship $[K_1 + K_2T_G - K_3P_A]$ where $T_G$ is said gas temperature signal and is indicative of the temperature of said gas in degree centigrade, $P_A$ is said pressure signal and is indicative of ambient pressure in millimeters of mercury, and $K_1$, $K_2$ and $K_3$ are constants.

5. A gas analysis system as in claim 1 in which said selected contaminant is a hydrocarbon, and said compensation means includes means for multiplying said output signal by the relationship $[K_1 + K_2T_G - K_3P_A]$ where $T_G$ is said gas temperature signal and is indicative of the temperature of said gas in degrees centigrade, $P_A$ is said pressure signal and is indicative of ambient pressure in millimeters of mercury, and $K_1$, $K_2$ and $K_3$ are constants.

6. A gas analysis system as in claim 1 and including means for sampling the exhaust gas from a motor vehicle to produce said sample gas.

7. A gas analysis system as in claim 1 in which said compensation means includes a digital computer.

8. A gas analysis system as in claim 1 in which said compensation means includes scaling amplifier means responsive to said gas temperature and pressure signals.

9. A method for measuring the amount of a selected contaminant in a gas sample comprising
   filling a sample cell with a sample gas,
   generating a rotating beam of infrared radiation,
   passing said beam of radiation alternately through said sample cell and a reference cell which contains a reference gas,
   measuring the absorption of said infrared beam by a selected contaminant in the gases contained within said sample and reference cells and producing electrical signals indicative thereof,
   computing from said electrical signals an output signal indicative of the amount of said contaminant in the sample gas,
   and compensating said output signal as a function of the temperature of said sample gas and as a function of ambient pressure.

10. A method as in claim 9 in which said selected contaminant is carbon monoxide, and in which the step of compensating said output signal includes the steps of
    measuring the temperature of said sample gas and producing a gas temperature signal $T_G$ indicative thereof,
    measuring the ambient pressure and producing a pressure signal $T_A$ indicative thereof,
    computing a correction signal according to the relationship $[K_1 + K_2T_G - K_3P_A]$ where $K_1$, $K_2$ and $K_3$ are constants,
    and multiplying said output signal by said correction signal.

11. A method as in claim 9 in which said selected contaminant is a hydrocarbon, and in which the step of compensating said output signal includes the steps of
    measuring the temperature of said sample gas and producing a gas temperature signal $T_G$ indicative thereof,
    measuring the ambient pressure and producing a pressure signal $T_A$ indicative thereof,
    computing a correction signal according to the relationship $[K_1 + K_2T_G - K_3P_A]$ where $K_1$, $K_2$ and $K_3$ are constants,
    and multiplying said output signal by said correction signal.

* * * * *